United States Patent
Wozencroft et al.

(10) Patent No.: US 9,566,159 B2
(45) Date of Patent: Feb. 14, 2017

(54) HIP RESURFACING

(75) Inventors: Robert Michael Wozencroft, Surrey (GB); Andrew Arthur Amis, London (GB); Justin Cobb, London (GB); Wael Dandachli, London (GB)

(73) Assignee: Imperial Innovations Ltd, London (GB)

( * ) Notice: Subject to any disclaimer, the term of this patent is extended or adjusted under 35 U.S.C. 154(b) by 646 days.

(21) Appl. No.: 12/998,578

(22) PCT Filed: Nov. 5, 2009

(86) PCT No.: PCT/GB2009/051488
§ 371 (c)(1),
(2), (4) Date: Jul. 29, 2011

(87) PCT Pub. No.: WO2010/052500
PCT Pub. Date: May 14, 2010

(65) Prior Publication Data
US 2011/0301654 A1 Dec. 8, 2011

(30) Foreign Application Priority Data

Nov. 5, 2008 (GB) .................................. 0820219.4

(51) Int. Cl.
*A61F 2/34* (2006.01)
*A61F 2/36* (2006.01)
(Continued)

(52) U.S. Cl.
CPC ......... *A61F 2/3603* (2013.01); *A61B 17/1668* (2013.01); *A61B 17/175* (2013.01);
(Continued)

(58) Field of Classification Search
CPC ....................................................... A61F 2/34
(Continued)

(56) References Cited

U.S. PATENT DOCUMENTS 4,324,006 A * 4/1982 Charnley .................. A61F 2/34
623/22.21
4,327,449 A * 5/1982 Charnley .................. 623/22.39
(Continued)

FOREIGN PATENT DOCUMENTS

EP 1 681 036 A1 A1 7/2006
EP 1 859 755 A2 A2 11/2007
(Continued)

OTHER PUBLICATIONS

International Search Report and Written Opinion mailed Aug. 19, 2010 for PCT/GB2009/051488 filed Nov. 5, 2009.
(Continued)

*Primary Examiner* — David Bates
*Assistant Examiner* — Olivia C Chang
(74) *Attorney, Agent, or Firm* — Wegman, Hessler & Vanderburg

(57) ABSTRACT

A method of locating an acetabular cup implant (100) in a pelvis comprises locating a plurality of reference points on the pelvis, defining a target location of the implant relative to the reference points, and placing the implant at the target location. A method of locating a femoral head implant (102) is also disclosed, together with associated guidance systems.

13 Claims, 25 Drawing Sheets

(51) Int. Cl.
*A61B 17/16* (2006.01)
*A61B 17/17* (2006.01)
*A61F 2/46* (2006.01)
*A61F 2/30* (2006.01)

(52) U.S. Cl.
CPC ............... *A61B 34/20* (2016.02); *A61F 2/34* (2013.01); *A61F 2/4609* (2013.01); *A61B 2034/2055* (2016.02); *A61B 2090/3983* (2016.02); *A61F 2002/30217* (2013.01); *A61F 2002/30616* (2013.01); *A61F 2002/30736* (2013.01); *A61F 2002/30878* (2013.01); *A61F 2002/349* (2013.01); *A61F 2002/3443* (2013.01); *A61F 2002/4627* (2013.01); *A61F 2002/4632* (2013.01); *A61F 2002/4685* (2013.01); *A61F 2230/0067* (2013.01)

(58) Field of Classification Search
USPC .................. 606/81, 91; 623/22.21–22.39
See application file for complete search history.

(56) References Cited

U.S. PATENT DOCUMENTS

| | | | |
|---|---|---|---|
| 7,927,338 B2 | 4/2011 | Laffargue et al. | |
| 2003/0153982 A1* | 8/2003 | Pria | 623/22.24 |
| 2004/0092944 A1 | 5/2004 | Penenberg | |
| 2005/0060040 A1* | 3/2005 | Auxepaules et al. | 623/22.18 |
| 2005/0203536 A1 | 9/2005 | Laffargue et al. | |
| 2005/0273176 A1* | 12/2005 | Ely | A61L 27/10 623/22.32 |
| 2006/0264969 A1 | 11/2006 | Leitner et al. | |
| 2008/0195221 A1* | 8/2008 | Howald | A61B 17/1635 623/22.32 |
| 2008/0306558 A1* | 12/2008 | Hakki | 606/86 R |
| 2009/0306679 A1* | 12/2009 | Murphy | 606/130 |
| 2010/0268348 A1* | 10/2010 | Ries et al. | 623/22.21 |

FOREIGN PATENT DOCUMENTS

| | | |
|---|---|---|
| JP | S56-18865 A A | 2/1981 |
| JP | 2005224613 A | 8/2005 |
| JP | 2006501972 A A | 1/2006 |
| WO | WO 2004/030559 A1 | 4/2004 |

OTHER PUBLICATIONS

International Preliminary Report on Patentability mailed May 19, 2011 for PCT/GB2009/051488 filed Nov. 5, 2009.
Office Action mailed Oct. 31, 2013 for Japanese Patent Application No. 2011-535168.
Second Office Action mailed Feb. 26, 2014 in Chinese Patent Application No. 200980153787.2.
Office Action mailed Jul. 3, 2014 in Japanese Patent Application No. 2011-535168.
Office Action mailed Nov. 26, 2015 for Japanese Patent Application No. 2011-535168.

* cited by examiner

HIP RESURFACING

CROSS-REFERENCE TO RELATED APPLICATIONS

This application claims the priority filing benefit of International PCT Application PCT/GB2009/051488 filed Nov. 5, 2009 and published under PCT 21(2) in the English language; and Great Britain Patent Application Serial No. 0820219.4 filed Nov. 5, 2008.

FIELD OF THE INVENTION

The present invention relates to the resurfacing of hips, and in particular to the design of hip resurfacing implants, guidance systems for use when resurfacing hips, and surgical tools for use when resurfacing hips.

BACKGROUND TO THE INVENTION

The morphology, orientation, and position of the acetabular and femoral components of the hip joint are important determinants of its function. The success of the native hip is based on design parameters of these components that, within a normal range of motion, avoid bony and soft tissue impingement. The native acetabulum is not perfectly hemispherical, and its rim is not simply a circle but rather a 3D shape with a series of prominences and depressions. Similarly on the femoral side, the junction between the head and the neck is not perfectly circular.

Modern hip resurfacing implant designs are based on a hemispherical acetabular cup with a level circular rim. On the femoral side, variable proportions of a sphere have been adopted by different implant manufacturers. It has been shown that acetabular cups that overhang the rim of the acetabulum are associated with impingement, early loosening and accelerated wear. This overhang would be expected when using a hemispherical cup, as part of its rim will be prominent in areas of low acetabular rim profile.

Determination of the 3D position of the acetabulum in the pelvis and the femoral head in relation to the femoral neck has continued to be a challenge. Antero-posterior acetabular position, which is not possible to quantify on plain radiographs, affects the function of the hip muscles. It may also be associated with impingement. Femoral head-neck relationship is similarly difficult to quantify.

SUMMARY OF THE INVENTION

The present invention provides a method of locating an acetabular cup implant in a pelvis comprising locating a plurality of reference points on the pelvis, defining a target location of the implant relative to the reference points, and placing the implant at the target location.

The reference points may be located by determining an absolute position of the pelvis, and analyzing images of the pelvis to determine the absolute positions of the reference points.

The present invention further provides a surgical guidance system comprising a locating device arranged to be placed in contact with the pelvis and to provide positional inputs indicating the position of the pelvis, processing means arranged to process the positional inputs and images of the pelvis, thereby to determine a target location for an acetabular cup implant, and a user interface arranged to provide a guide to guide a user to place the cup implant in the target location.

The processing means may be arranged to identify reference positions on at least one image of the pelvis and to determine the target location relative to the reference points. The system may further comprise user input means arranged to enable a user to locate the reference positions on the image.

The present invention further provides a method of locating a femoral head resurfacing implant on a femur, the method comprising locating a plurality of reference points on the femur, defining a target location of the implant relative to the reference points, and placing the implant at the target location.

The reference points may be located by determining an absolute position of the femur, and analyzing images of the femur to determine the absolute positions of the reference points.

The present invention further provides a surgical guidance system comprising a locating device arranged to be placed in contact with a femur and to provide positional inputs indicating the position of the femur, processing means arranged to process the positional inputs and images of the femur to determine a target location for a femoral resurfacing implant, and a user interface arranged to provide a guide to guide a user to place the implant at the target location.

The processing means may be arranged to identify reference positions on at least one image of the femur and to determine the target location relative to the reference points. The system may further comprise user input means arranged to enable a user to locate the reference positions on the image.

The present invention further provides an acetabular cup implant comprising a part-spherical cup the rim of which varies in height around the cup so as to define a recess for location between the pubis and the ischium. The rim may define at least one recess. It may define three recesses. One of the recesses may be deeper than the other two. The deeper recess may be arranged to correspond to the acetabular notch, and to be located between the ischium and the pubis. The bottom of the deeper recess may be at least 20° below a reference plane through the cup centre and parallel to a best fit, for example a least squares best fit, plane through the rim. The bottom of the shallower recesses may be at least 10° below the reference plane.

The cup may be part spherical by virtue of its inner surface being part spherical, or its outer surface being part spherical, or both its inner and outer surfaces being part spherical. For example the inner surface may be part spherical and the outer surface may be non-spherical.

The rim of the cup may have an inner edge and an outer edge and the variations in height around the rim at the inner edge may be different from the variations in height at the outer edge. The variations in height may be less at the inner edge than at the outer edge. The variations in height at the inner edge may be substantially zero. The number or the angular position of the eminences or recesses at the inner edge may be different from the corresponding number or angular position at the outer edge. The cup may have an outer surface having a main bone interface region arranged to contact the bone of a pelvis and an extension region arranged to extend beyond the superior edge of the acetabulum. The extension region may have at least one different property from the main bone interface region. The property may be radius of curvature or surface texture. For example the extension region may be less rough than the main region. The extension region may be rough only on a scale which is smaller than a scale on which the main region is rough.

The present invention further provides a femoral resurfacing implant comprising a bearing portion with a part spherical outer surface and support means for supporting the implant on the femur, wherein the rim of the bearing portion varies in height around the bearing portion. The bearing surface may have two extended regions where the surface extends further round the femur than in to recesses between the extended regions. Each of the extended regions may subtend an angle of at least 10° greater than each of the recesses to either side of it, an in this case at least 15° greater.

The present invention further provides a machining tool for machining a femur in preparation for resurfacing, the tool comprising a location member for location in the femur, a cutter for cutting the femur, support means arranged to support the cutter and to allow the cutter to be rotated about the location member, and a cam system arranged to control movement of the cutter in an axial direction as it is rotated about the locating member so as to vary the depth to which the femur is cut.

The present invention further provides a tool for manipulating an acetabular cup implant, the tool comprising: a flexible member having a cavity formed within it, a domed front surface arranged to fit inside the implant, and sealing means around the domed surface arranged to seal against the inside of the implant; rigid support means for supporting the rear of the flexible member; and pulling means arranged to pull a portion of the flexible member away from the implant to cause a partial vacuum between the implant and the flexible member to secure the implant to the flexible member.

Some embodiments of the invention can therefore provide any one or more of the following:
a method for orienting an acetabular implant in the relation to the pelvis specific for pelvic morphology and gender;
a method for locating the acetabular cup in relation to the pelvis specific for pelvic morphology and gender;
a shape of acetabular cup that both minimizes soft tissue damage from overhanging metal edges in the socket and maximizes femoral head coverage and pelvic bone support;
a shape of acetabular cup that optimizes load transfer, to minimize wear;
a shape of acetabular cup that has an ilio-pubic recess for the psoas tendon of a shape and position defined by the algorithm;
a shape of acetabular cup that includes an ischial 'facet' to increase surface area and enhance stability in flexion;
a method for orienting the femoral head implant in relation to the femur specific for femoral morphology and gender;
a method for locating the femoral head implant in relation to the femur specific for femoral morphology and gender;
a shape of femoral component that minimizes soft tissue and blood vessel damage to the underlying femoral head and adjacent femoral neck posterosuperiorly;
a shape of femoral head implant that minimizes the risk of fracture of the femoral neck due to notching anterosuperiorly in cam type hip deformity;
a shape of femoral head implant that has an extended flexion and extension facet;
an internal shape that can accommodate the relative anterosuperior deficiency in cam type hip deformity by having an internal cavity that is partially filled-in so as to effectively substitute for that portion of the bone that is missing.

The present invention provides a novel anatomic design of the acetabular cup. A reliable method for accurately positioning the acetabular cup in the pelvis is also provided. The present invention can help to provide an optimally placed anatomic hip device providing an optimum range of motion without the risk of impingement and associated with low wear rates.

Preferred embodiments of the present invention will now be described by way of example only with reference to the accompanying drawings.

DESCRIPTION OF THE PREFERRED EMBODIMENTS

Acetabulum

CT scans of 22 normal acetabula were analysed using 3D reconstruction software. These included 12 dry cadaveric innominate bones containing normal acetabula. In addition post-operative CT scans from 12 patients with unilateral acetabular fractures were used to analyse the normal contralateral acetabulum. The mean age of these patients was 38.4 years (range 22-61 years). There were five females and seven males. The gender of the cadaveric bones was not known.

Figure 1:
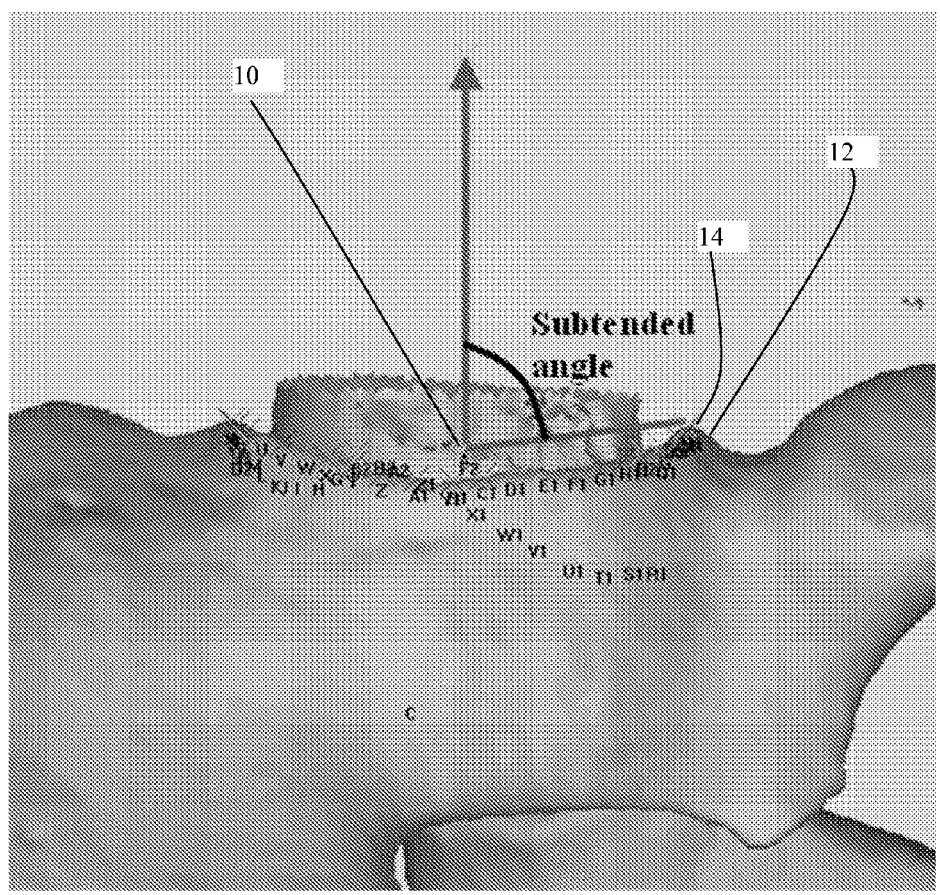
FIG. 1 is a profile view of an acetabulum showing markers used to determine the shape of the acetabular rim.
Figure 2:
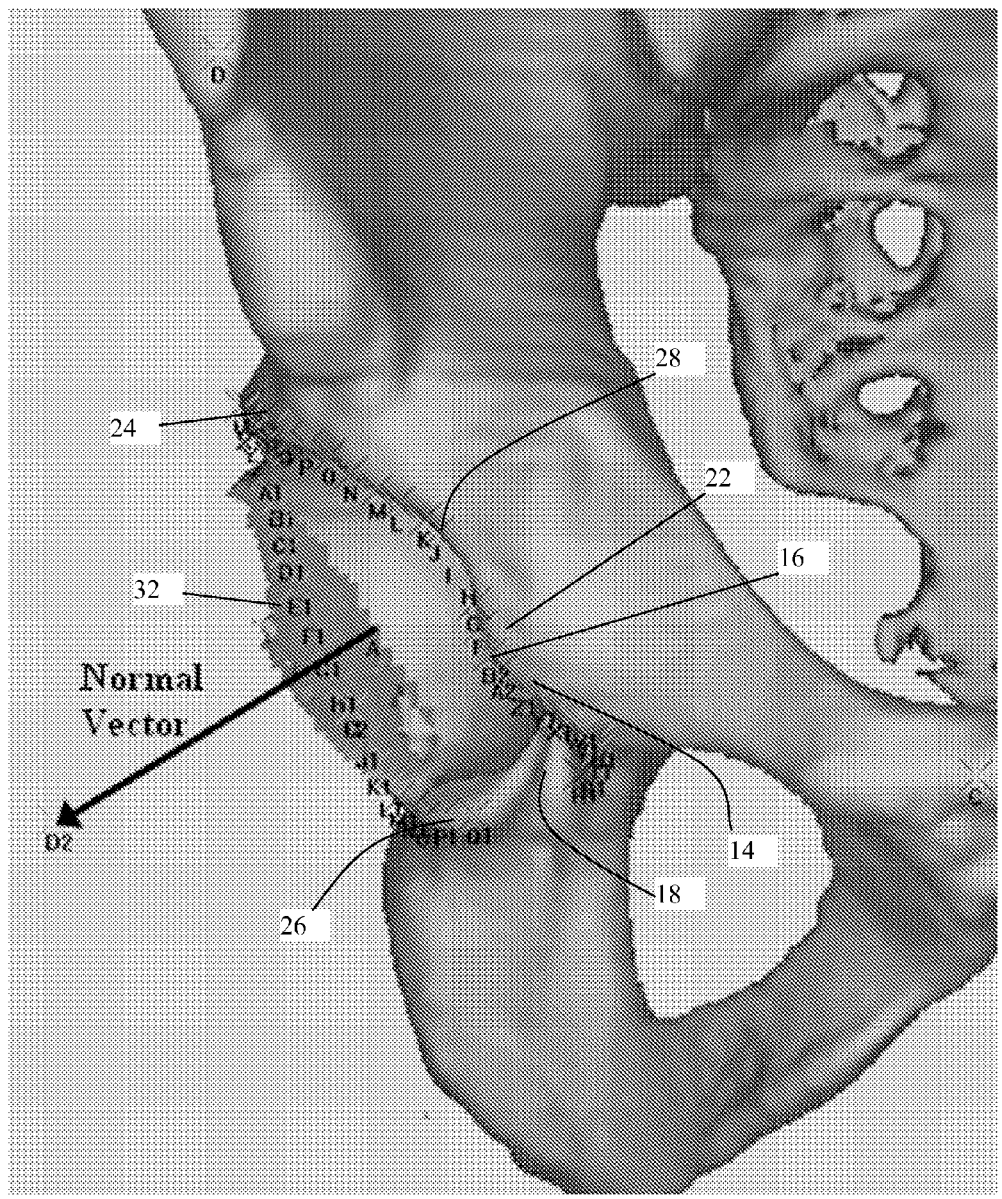
FIG. 2 is an anterior view of the acetabulum of FIG. 1.
Figure 3:
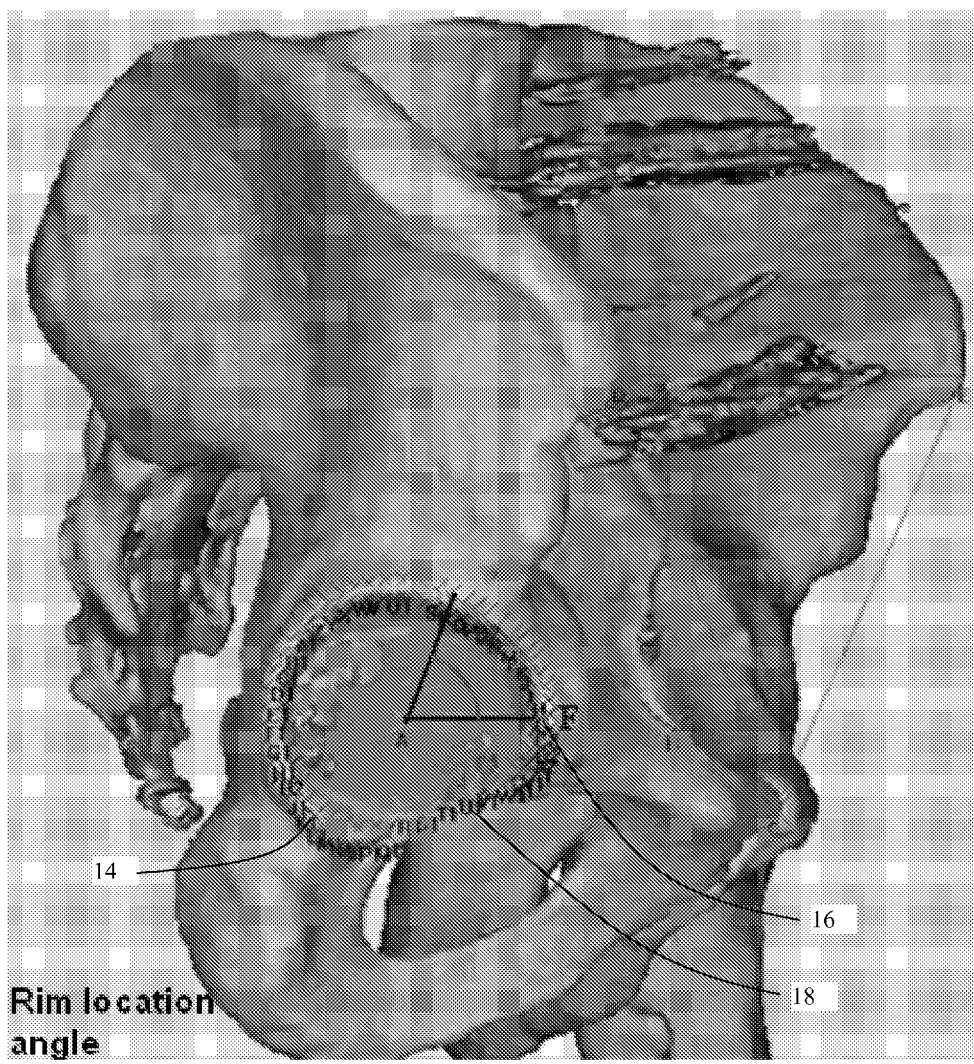
FIG. 3 is a lateral view of the acetabulum of FIG. 1.
Figure 4:
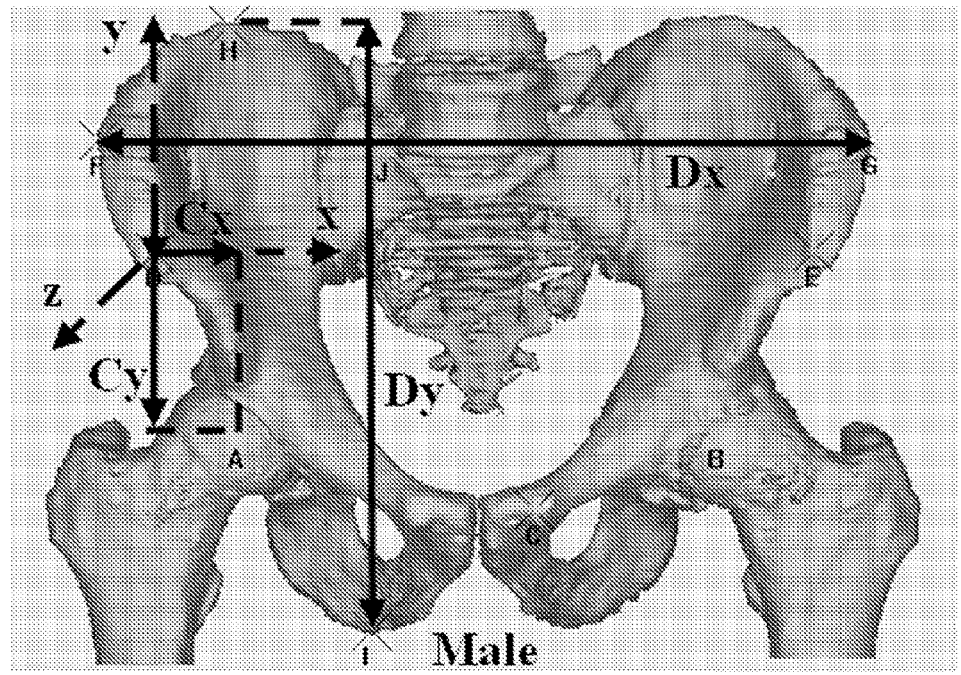
FIG. 4 is an anterior view of a male pelvis.
Figure 5:
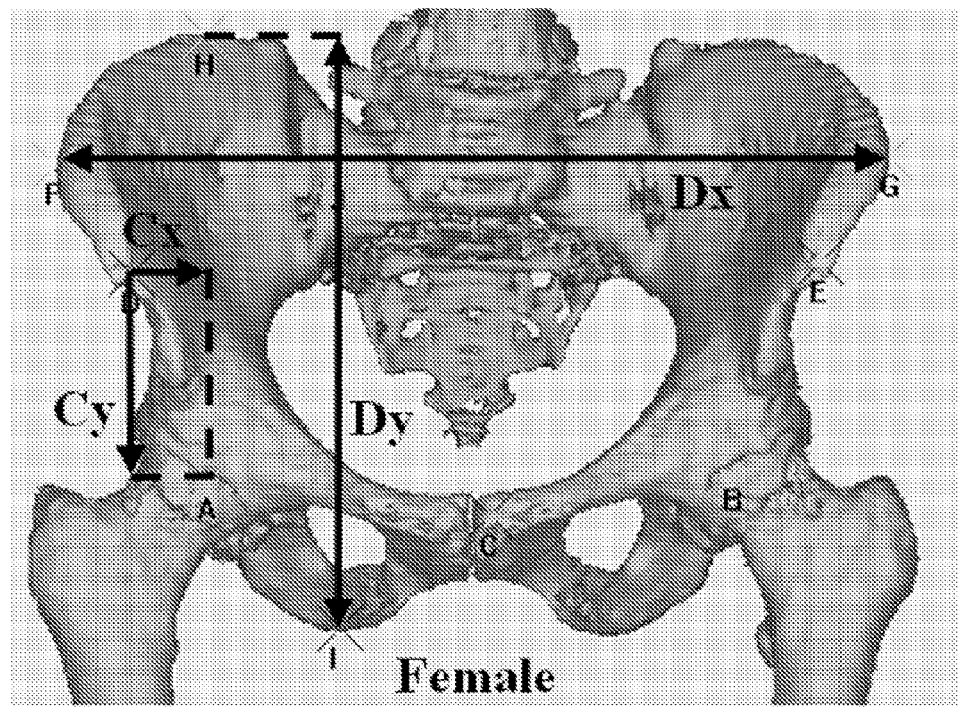
FIG. 5 is an anterior view of a female pelvis.
Figure 6:
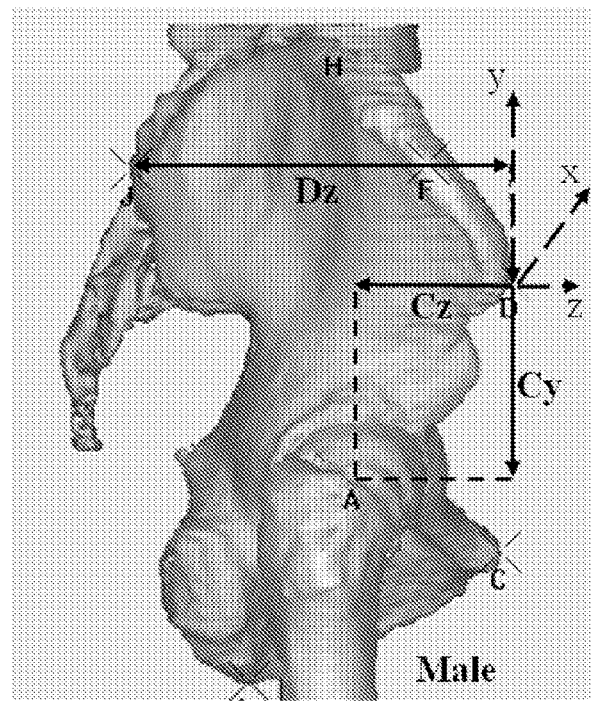
FIG. 6 is a lateral view of the male pelvis.
Figure 7:
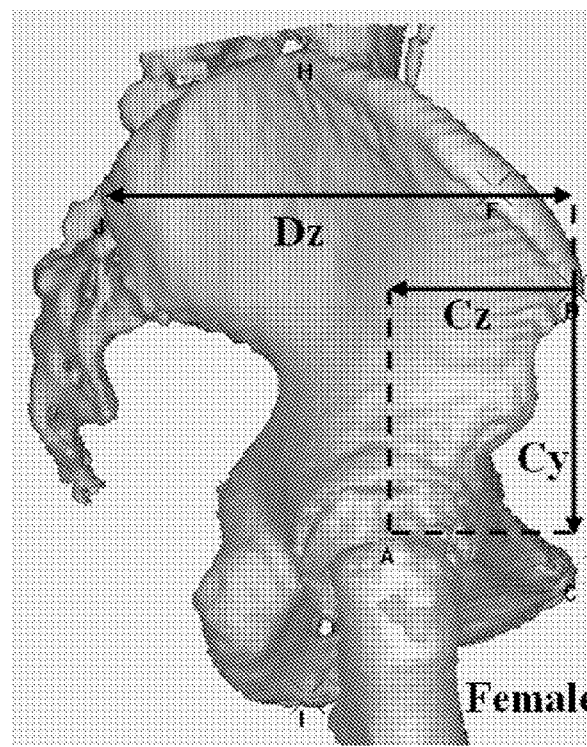
FIG. 7 is a lateral view of a female pelvis.
Figure 17:
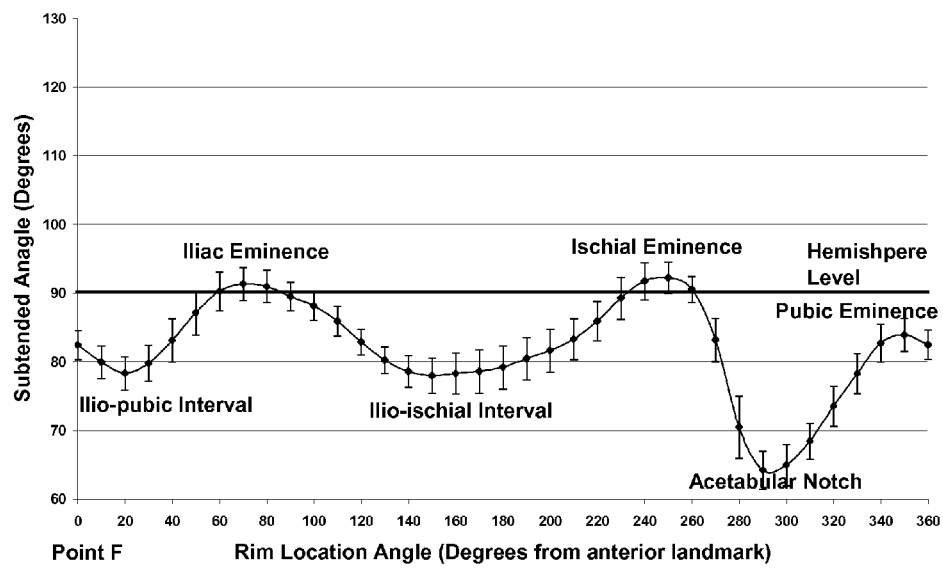
FIG. 17 shows profiles of a number of acetabular rims.

Referring to FIGS. 1 to 3 the centre 10 of the acetabulum 12 was defined as the centre of a best-fit sphere fitted through points in the articulating part of the acetabular socket; i.e. the lunate surface. Markers, indicated on the drawings as A-Z, A1-Z1 etc, were then assigned to respective points around the whole of the acetabular rim 14 starting from the pubic end 16 and moving postero-superiorly. The acetabular notch 18 was also included in order to complete the cycle. A best fit plane was then fitted through all the rim points except the ones on the acetabular notch 18. This plane defined the acetabular plane, and the normal to it at the acetabular centre formed the normal vector D2. The angle subtended between this normal vector and the line joining the centre and a rim point defined the subtended angle for that particular point as shown in FIG. 1. The angular location of the rim points was measured in relation to an anterior rim landmark obtained after aligning the pelvis with the anterior pelvic plane (APP) defined by the two anterior superior iliac spines (ASIS) and the pubic tubercles. This provided a 'clock' position for each of the rim points. A 2D profile of the acetabular rim, showing subtended angle as a function of 'clock' position, was therefore generated with accurate referencing in relation to the anterior landmark. This is shown in FIG. 17 and discussed below.

Six landmarks were then identified which defined the peaks and troughs of the acetabular rim. Those were namely the highest points on the pubic 22, iliac 24 and ischial 26 eminences and the lowest points in the ilio-pubic interval 28, the posterior rim 30 and the acetabular notch 18. The subtended angles for these points were noted and, together with the 2D profile of the acetabulum, were compared with the results obtained by a second independent observer to check the method's reliability.

Gender-Specific 3D Acetabular Positioning

Referring to FIGS. 4 to 7, computerised tomography scans of thirty-seven hips (19 female and 18 male) were analysed using 3-D reconstruction software. The anterior pelvic plane (APP), defined by the two anterior superior iliac spines (ASIS) and the pubic tubercles, was used as the basis of the coordinate system with the origin set at the right anterior superior iliac spine. The x-axis pointed horizontally from left-to-right, the y-axis vertically upwards, and the z-axis posterior-to-anterior. The femoral head centre represented the hip centre and its coordinates $(Cx, Cy, Cz)$ were measured.

After aligning the pelvis with the anterior pelvic plane, the pelvic horizontal dimension (Dx) was defined as the distance between the most lateral points F, G on the iliac crests, and its vertical dimension (Dy) was the distance between the highest point H on the iliac wing and the lowest point I on ischial tuberosity. The pelvic depth (Dz) was defined as the horizontal distance between the posterior superior iliac spine J and the ipsilateral anterior superior iliac spine D.

Figure 8:
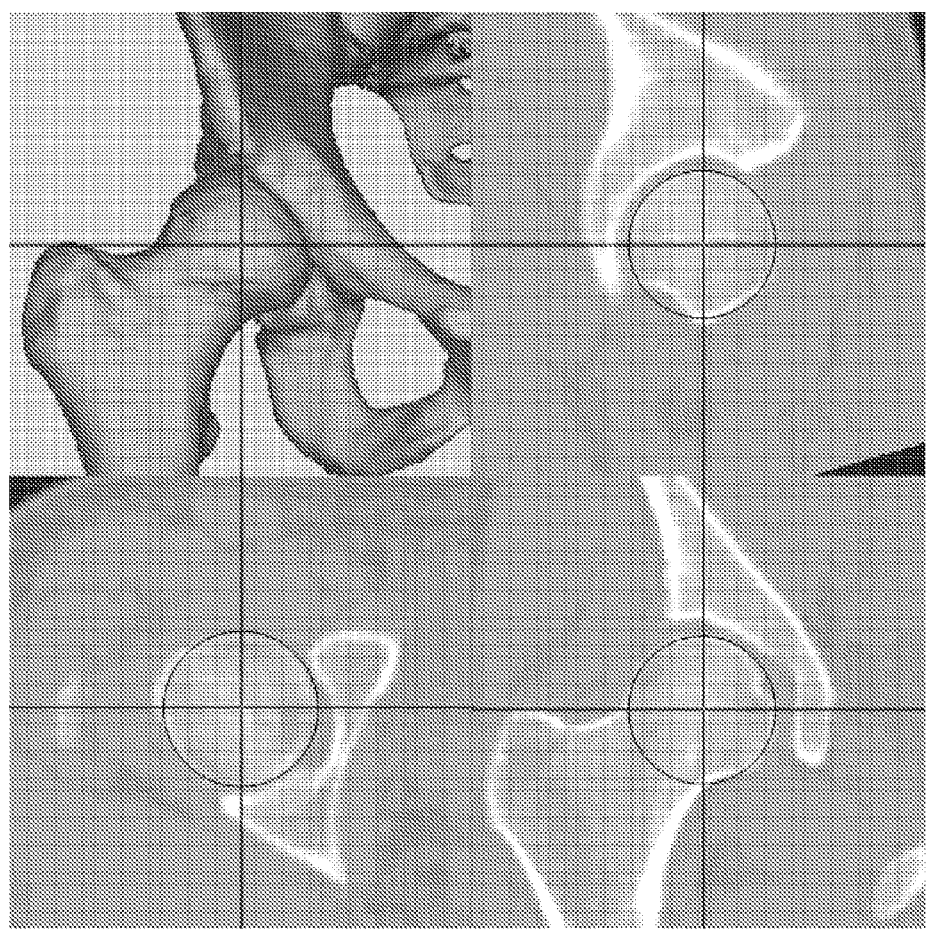
FIG. 8 shows location of the hip centre using orthogonal CT views.
Figure 18:
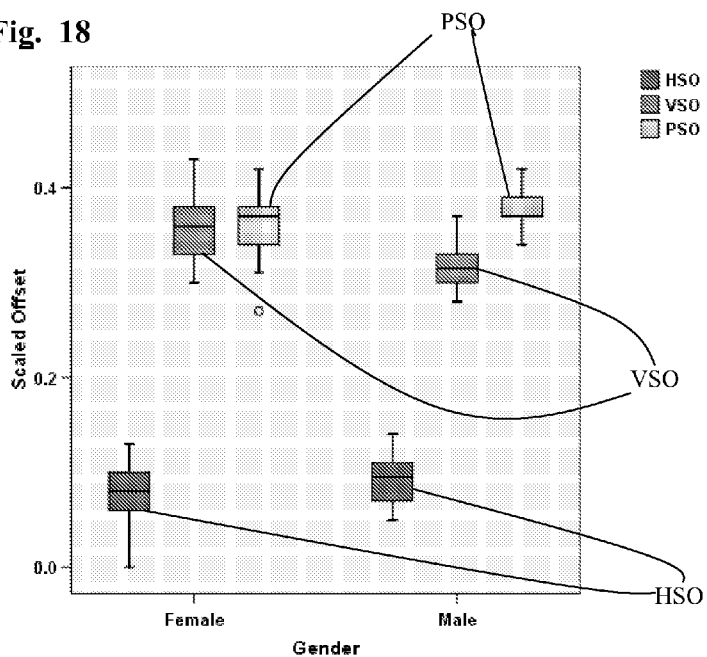
FIG. 18 is a chart showing distributions of horizontal, vertical and posterior scaled offsets of a number of hip centres.

Referring to FIG. 8 the hip centre was determined by using the three orthogonal slices from the CT scan. Its x, y, and z coordinates were measured in relation to the reference coordinate system described above. The ratios of these coordinates to their corresponding pelvic dimensions $(Cx/Dx, Cy/Dy, Cz/Dz)$ were measured. These ratios represent the horizontal, vertical, and posterior scaled offsets and have been termed herein HSO, VSO, and PSO respectively. The results were analysed for males and females. These are shown in FIG. 18 and discussed below.

Twenty-four points were then defined around the superior half of the acetabular rim, which is the load bearing part of the acetabulum, and a best-fit acetabular plane through these points created. This set of points was acquired separately, though a sub-set of the points of FIGS. 1 to 3 could have been used. The inclination and anteversion of the acetabular plane in relation to the anterior pelvic plane FOR were measured for both groups. An independent observer then repeated the landmark acquisition and the measurements for all the scans in order to test the method's reliability.

The Femur

CT scans of seven normal hips were analysed with 3D reconstruction software. The centre of the femoral head was then determined by fitting a sphere through a set of points on the femoral head surface.

Figure 9:
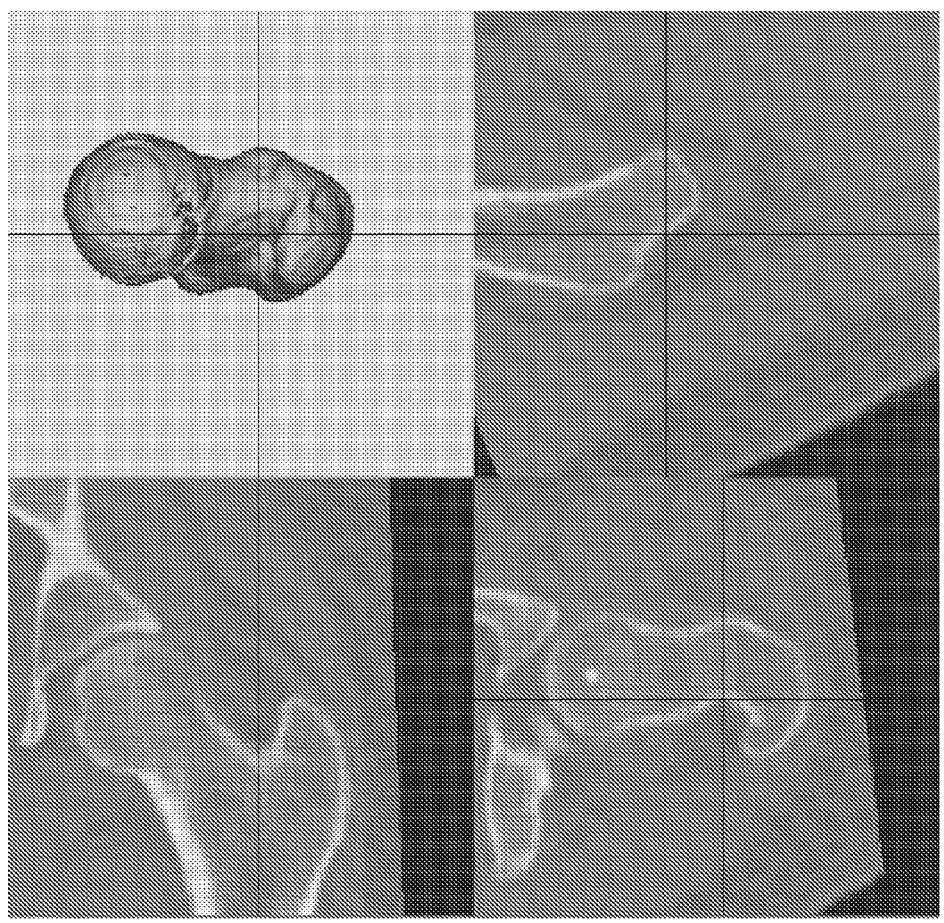
FIG. 9 shows location of a reference point on the femur using orthogonal CT views.

Referring to FIG. 9, a reference point, indicated by the cross on each scan of FIG. 9, was assigned to the medial edge of the piriform fossa.

Figure 10:
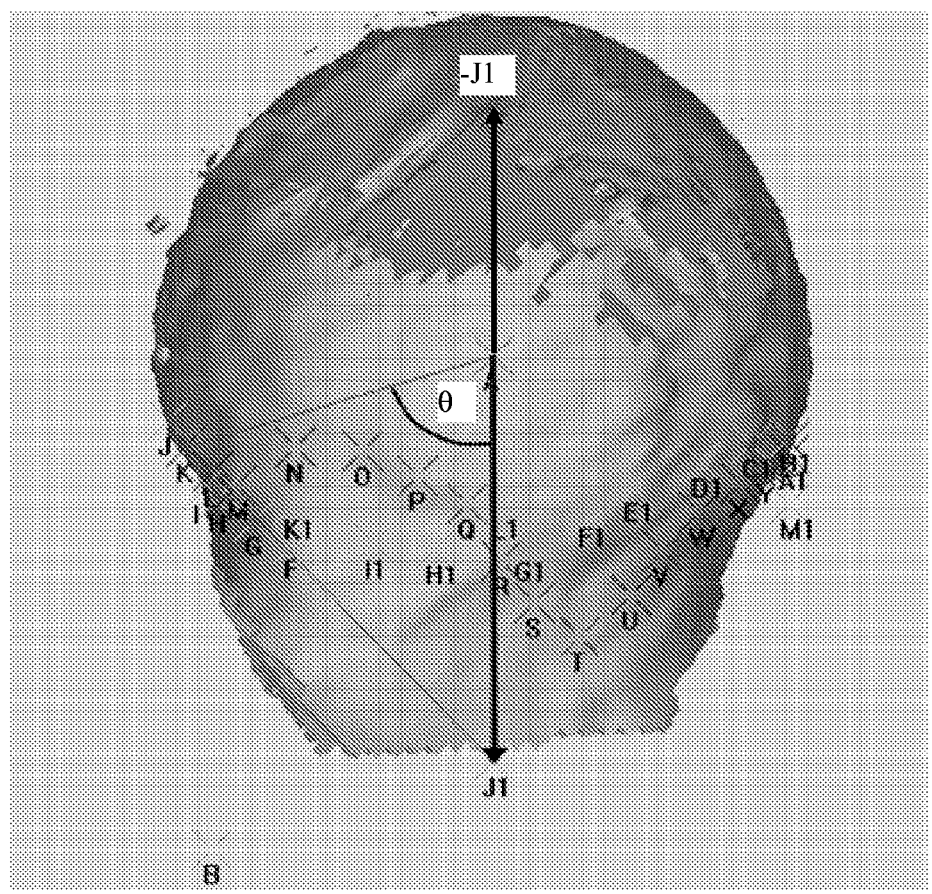
FIG. 10 is an anterior view of the head of a femur showing markers on the head-neck junction.
Figure 11:
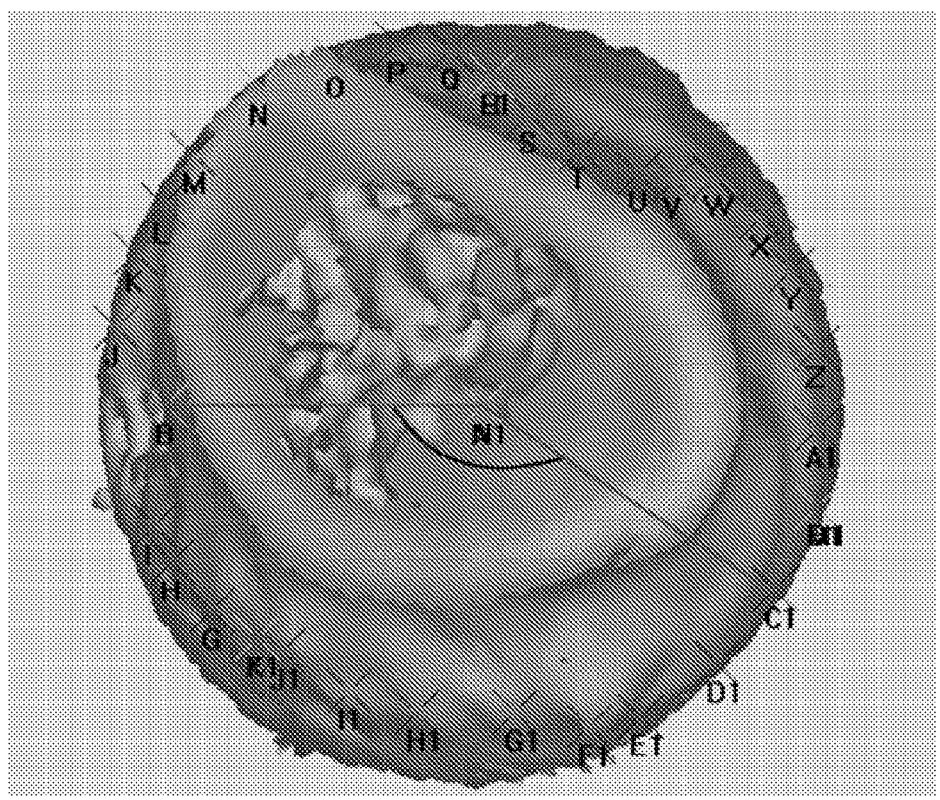
FIG. 11 is an inferior view of the femoral head showing 'clock' positions for the markers of FIG. 10.

Referring to FIGS. 10 and 11, points, marked by letters in FIGS. 10 and 11, were assigned on the femoral head-neck junction starting from the level of the piriform fossa reference point in an anterior direction. A combination of the 3D view and the three orthogonal 2D views from the CT scans was used for that purpose. A best fit plane through the head-neck junction points was determined, and the downward perpendicular to that plane at the head centre A defines the normal vector J1 to the plane. For each point, the angle subtended was defined as the angle at the head centre between the point and the upward normal (−J1) to the plane at the head centre. Therefore the angle (180−θ) between this upward normal vector (−J1) and a line joining the head centre to a head-neck junction point (e.g. point K as shown in FIG. 10) defines the subtended angle of that point.

Figure 19:
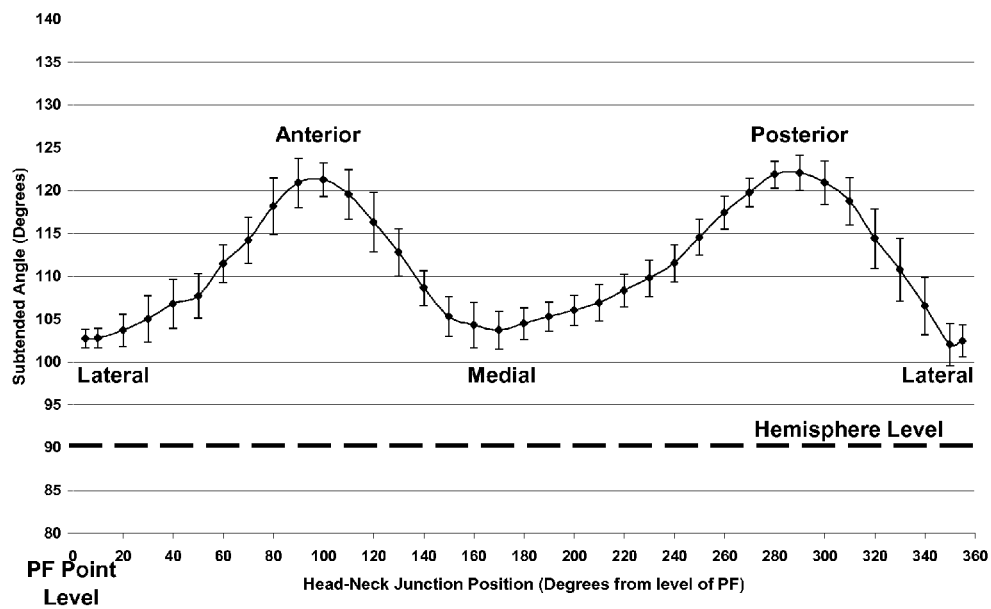
FIG. 19 shows profiles of a number of femoral head/neck junctions.

Referring to FIG. 11, the angular position of the points on the head-neck junction was measured in relation to the piriform fossa reference point B. The 'clock' position angle (about the normal vector, in the head-neck junction plane) was measured for all the head-neck junction points, and a plot of the subtended angle as a function of this 'clock' position angle maps out the head-neck junction. This is shown in FIG. 19 and discussed below.

Femoral Head 3D Positioning

Figure 12:
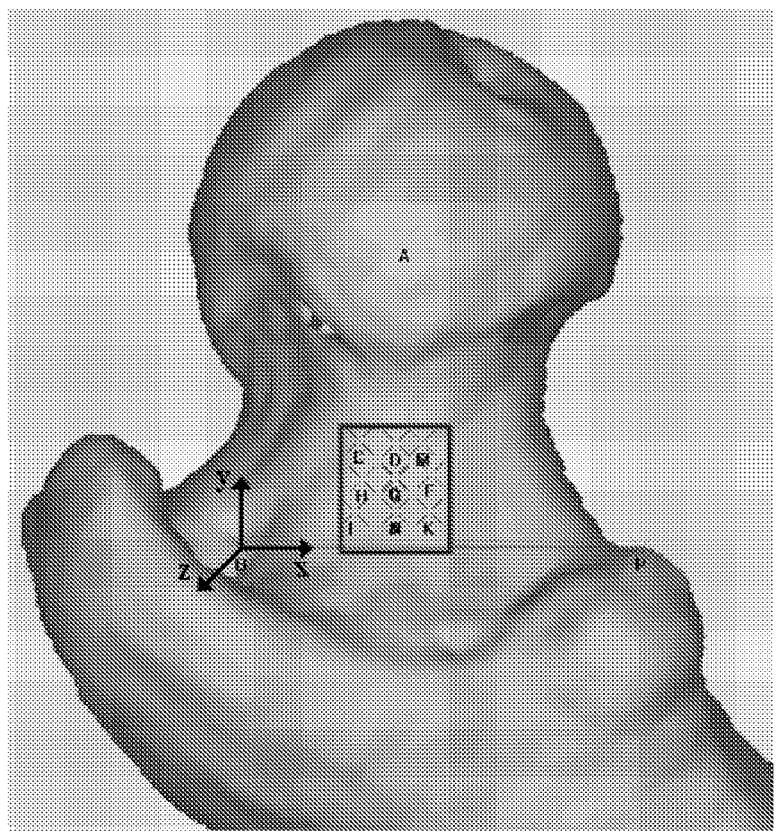
FIG. 12 is a posterior view of the femoral head showing reference points on the femoral neck.
Figure 13:
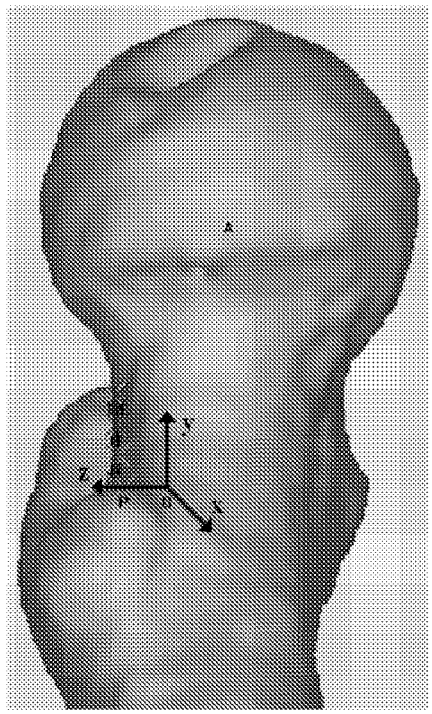
FIG. 13 is a medial view of the femoral head showing reference points of FIG. 12.
Figure 14:
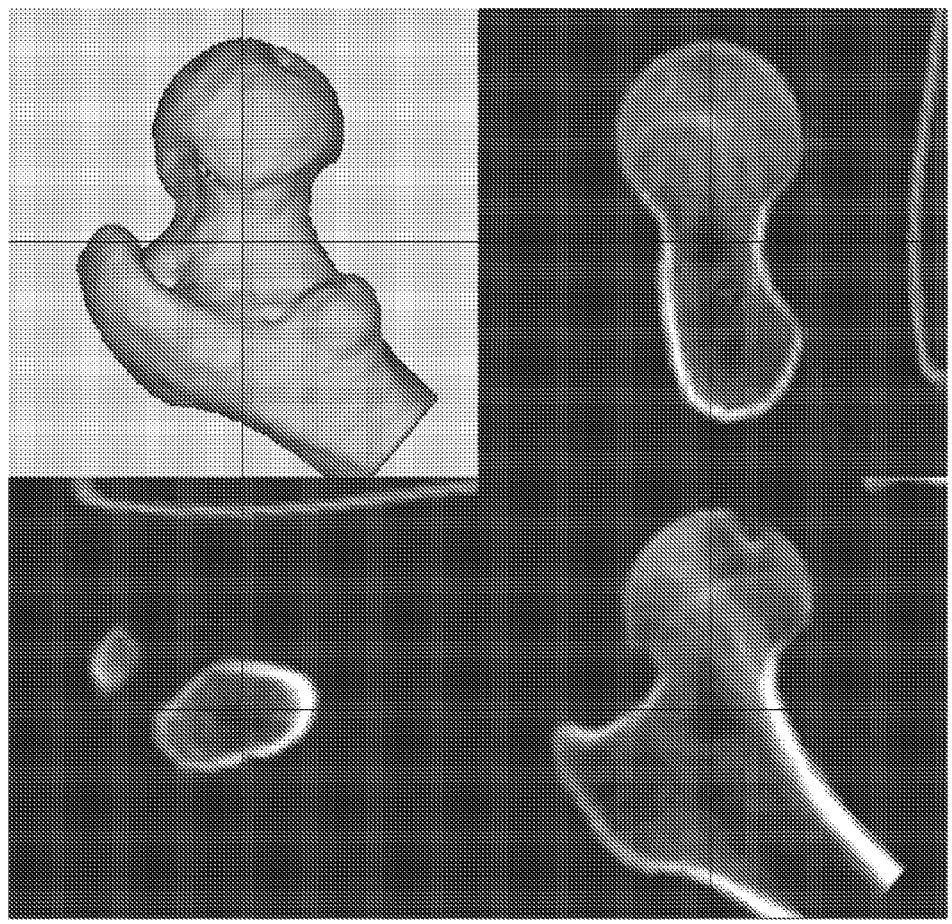
FIG. 14 shows location of the femoral neck centre from orthogonal CT views.
Figure 15:
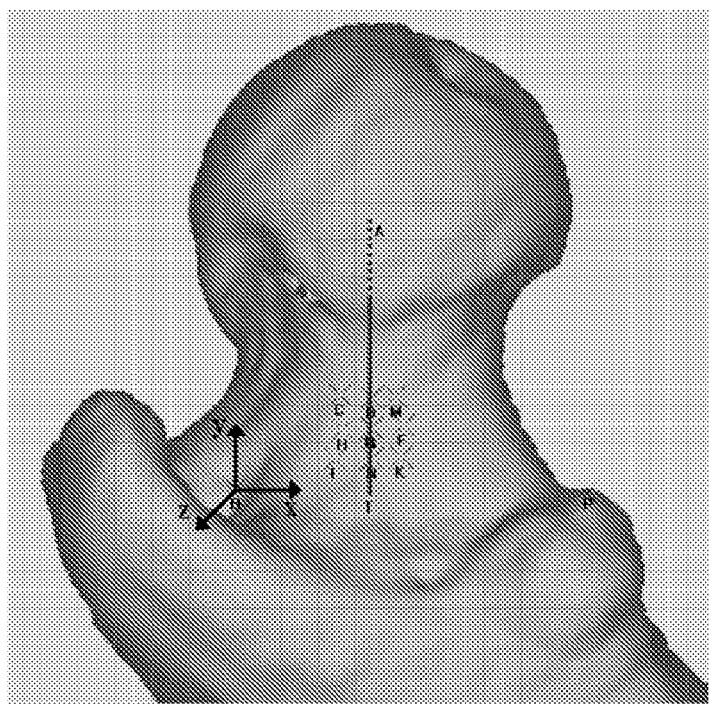
FIG. 15 is a posterior view of the femoral head showing location of the neck axis.
Figure 16:
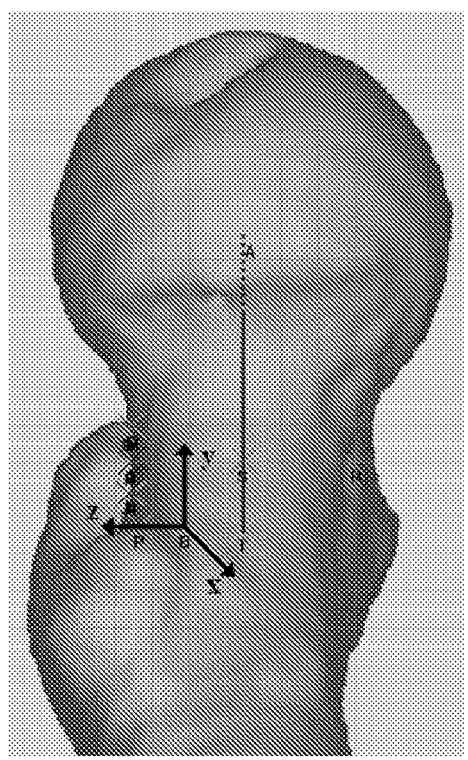
FIG. 16 is a medial view of the femoral head showing location of the neck axis

Referring to FIGS. 12 and 13, CT scans of 26 dry cadaveric femora were analysed using the same 3D reconstruction software. The centre A of the femoral head was defined as the centre of a best fit sphere through points on the head surface. For a standardised orientation, a reference plane, defined by a best fit plane through points on the flat part of the posterior surface of the femoral neck, was used. The point B was reproducibly acquired on the medial edge of the piriform fossa in the proximal femur. Another point P was identified at the highest point on the lesser trochanter after aligning the femur with the posterior neck reference plane. Aligning the line joining these two points B, P horizontally completed the process of standardised orientation of the femur. A coordinate system was then defined with the origin at the point B, the X axis along the line BP, the Y axis perpendicular to the X axis in the posterior neck reference plane, and the Z axis perpendicular to the X and Y axes.

The mean of the points on the posterior neck plane was identified and the neck centre at the level of this mean point determined using the sagittal and coronal images. The neck centre was taken to be the point, on the perpendicular to the neck plane, half way between the mean point on the neck plane and the point R on the opposite side of the neck. This point will be referred to as the neck centre (NC).

With the femoral neck in the plane of the screen, the vertical projection of the neck centre NC perpendicular to the line BP (joining the piriform fossa B and lesser trochanter P points (the base-of-neck line)) was then determined, inset from line BP, by the same offset as NC. This point is the base of neck centre, and the line joining this point and the neck centre defines the neck axis The varus/valgus and ante-/retro-version relationships between the femoral head and neck can then measured. With the origin of the proximal femoral frame of reference set to the piriform fossa point B, the x,y,z-coordinates of the head centre can be calculated.

The landmark acquisition and measurements were repeated by an independent observer in order to test the method's reliability.

Results

The Acetabulum

Acetabular Rim Morphology

The acetabulum is a complex structure that cannot be simply represented by a hemisphere. The measurements described above found a repeatable pattern in its rim with identifiable peaks and troughs on the 2D profile as shown in FIG. 17. This figure shows profiles of some of the acetabula studied, based on plots of the subtended angle of individual rim points as a function of their 'clock' position angle. Deviations from a hemisphere can be seen in relation to a subtended angle of 90°, with a higher subtended angle indicating less than a hemisphere.

The subtended angles and 'clock' position angles for the eminences and troughs on the acetabular rim were noted (Table 1). Important features include the cut-out in the ilio-pubic interval, referred to as the acetabular notch, which accommodates the ilio-psoas tendon, and the augmentation at the ischial eminence which may provide stability in flexion. There is also an iliac eminence in the region of the ilium and a pubic eminence in the region of the pubis. An ilio-ischial interval or trough is formed between the ischium and ilium and an ilio-pubic interval or trough between the ilium and pubis. These last two intervals are not as deep as the acetabular notch.

TABLE 1

Subtended angles and 'clock' position angles for the rim points at the eminences and troughs of the acetabular rim.

| Rim Locus | Subtended Angle (Deg) | | Rim Location Angle (Deg) | |
|---|---|---|---|---|
| | Mean | SD | Mean | SD |
| Pubic Eminence | 88 | 4 | 348 | 5 |
| Ilio-pubic trough | 81 | 4 | 20 | 8 |
| Iliac Eminence | 95 | 3 | 68 | 9 |
| Ilio-ischial trough | 81 | 4 | 147 | 13 |
| Ischial Eminence | 96 | 3 | 244 | 6 |
| Acetabular Notch | 62 | 6 | 287 | 7 |

The morphology of the acetabular rim takes into account certain bony and soft tissue anatomical considerations. An important element of those is the trough in the iliopubic interval which accommodates the ilio-psoas tendon. This cutout is crucial to avoid impingement in flexion. Superior coverage is evident by the iliac eminence, and when this is deficient as is the case in dysplasia. Moreover, the ischial prominence probably plays an important role in providing adequate coverage as in squatting, for instance. Reconstructive surgery according to some embodiments of the present invention aims to restore these features.

Figure 17A:
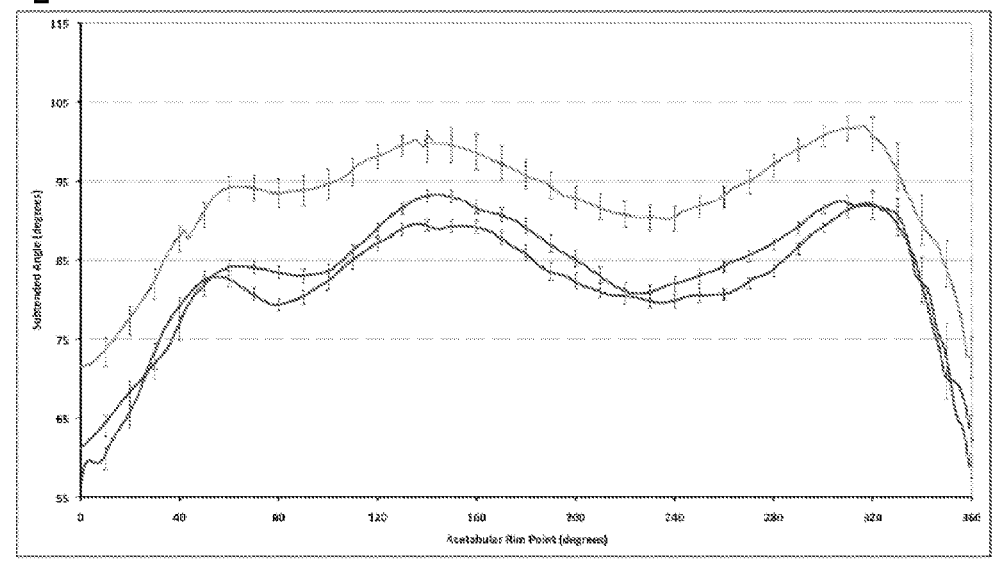
FIG. 17a shows profiles of acetabular rims of different types of hip.

FIG. 17a shows similar plots of the acetabular rim shape for three different groups of hips of three respective types. In this case angles are measured from the bottom of the acetabular notch. The upper profile is of pincer-type hips, the middle profile of normal hips and the lower profile of cam-type hips. These plots are relevant as they show that, while the absolute height of the rim varies between different types of hip, the shape of the profile is essentially the same in all three types of hip. This means that a single implant can be designed for reconstruction of different types of hip.

Acetabular 3D Positioning

The scaled offsets of the hip centre vary predictably between genders, and for a given individual of known gender its coordinates can be derived from known pelvic landmarks. The scaled offsets for males and females are shown in Table 2.

TABLE 2

The hip centre scaled offsets expressed as the means and their 95% confidence intervals. The p values for the gender differences are also shown. HSO, VSO, and PSO are the horizontal, vertical, and posterior scaled offsets respectively.

| Scaled Offset | Female | Male | p Value |
|---|---|---|---|
| HSO | 0.08 (±0.018) | 0.10 (±0.014) | 0.043 |
| VSO | 0.35 (±0.018) | 0.32 (±0.015) | 0.002 |
| PSO | 0.36 (±0.017) | 0.38 (±0.013) | 0.031 |

The results were scrutinized for gender differences in the scaled offsets by using the two-sample student t-test assuming unequal variances. There was a statistically significant difference in all three scaled offsets. FIG. 18 is a chart showing the distributions of the hip centre scaled offsets HSO, VSO, and PSO.

The Femur:

Femoral Head-Neck Junction Morphology

The femoral head is more than a hemisphere. The proportion of a sphere that it makes varies along its rim or junction with the femoral neck. A 2D profile was created by plotting the subtended angles of the head-neck junction points as a function of their 'clock' position angles on the head-neck junction and this is shown in FIG. 19.

It can be seen that there is a pattern to the femoral head-neck junction. Anterior and posterior 'extensions' of the head provide an extra space for articulation with the acetabulum, whereas 'cut-outs' medially and laterally avoid impingement, and allow the blood vessels to enter the head posterolaterally.

Femoral Head-Neck Frame of Reference

The position and orientation of the femoral head can be accurately defined relative to the femoral neck. Using the proximal femoral frame of reference of FIGS. 12 and 13 which is dependent on the neck, a standardised and reproducible orientation of the femur can be achieved. From the origin at the piriform fossa, x-, y-, and z-coordinates for the femoral head centre can be measured, and the position of the head centre and orientation of the head using the head-neck junction plane, both relative to the neck axis, can be quantified in 3D space.

Implant Design

Figure 20:
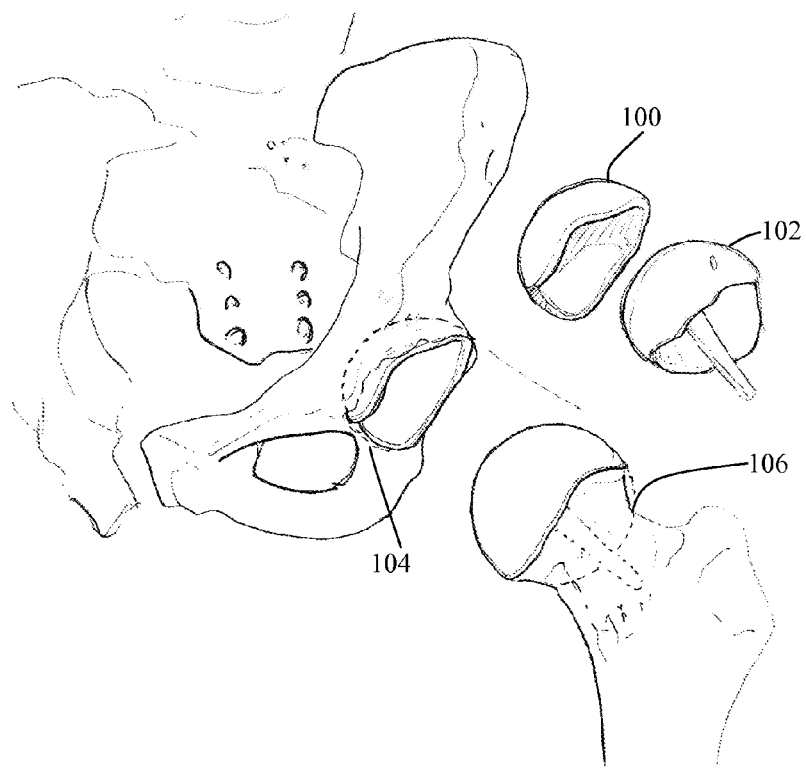
FIG. 20 is a perspective exploded view of a hip, and femoral and acetabular implants according to an embodiment of the invention.

Referring to FIG. 20, a hip re-surfacing implant set comprises an acetabular cup 100 for resurfacing the acetabulum 104 and a femoral head implant 102 for resurfacing the head of the femur 106.

Figure 21:
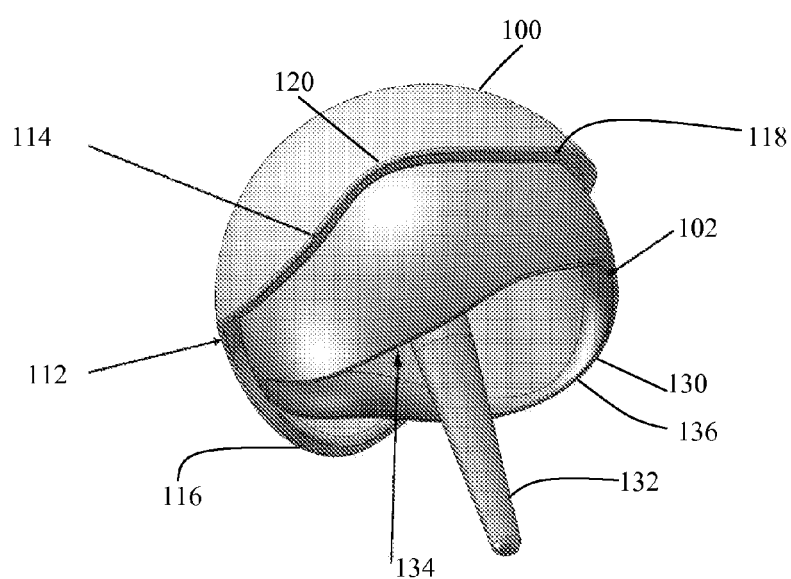
FIG. 21 is an anterior view of the implant set of FIG. 20.
Figure 22:
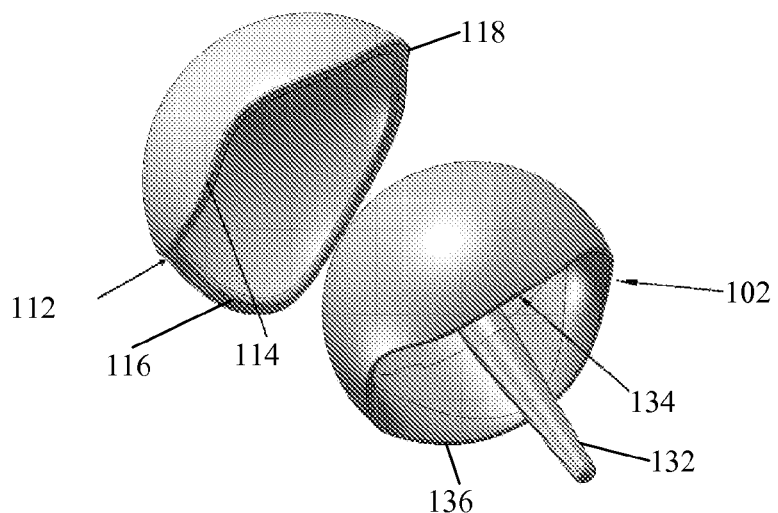
FIG. 22 is an anterior view of the implants of FIG. 21 separated.
Figure 23:
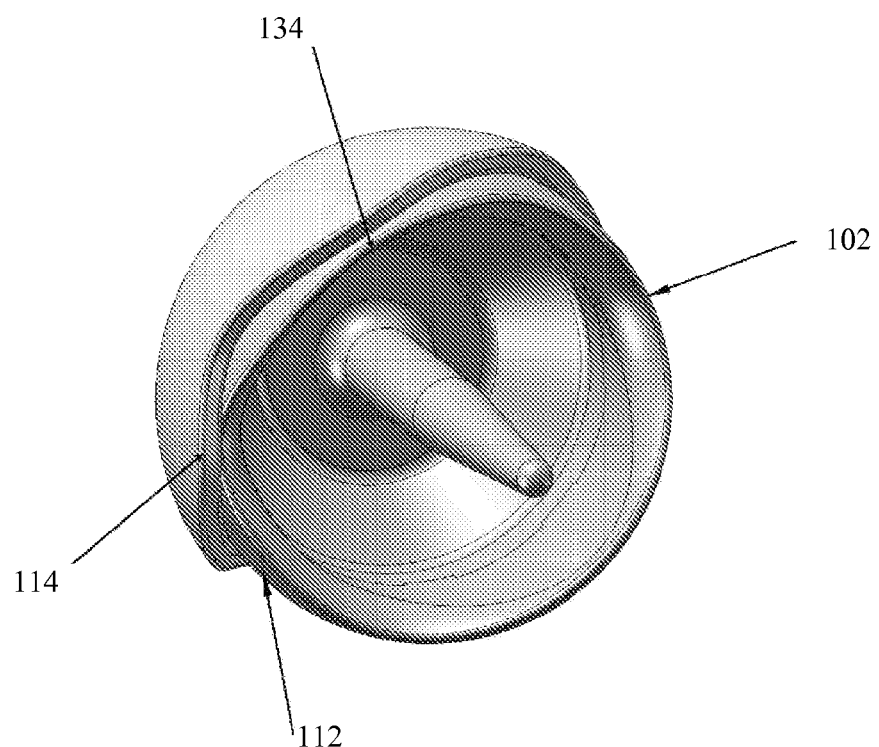
FIG. 23 is a further perspective view of the implants of FIG. 20.
Figure 24:
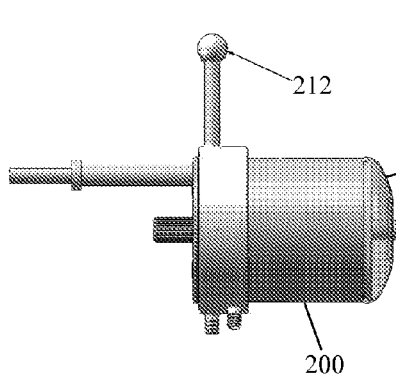
FIG. 24 is a side view of machining tool according to an embodiment of the invention for a femoral head.
Figure 25:
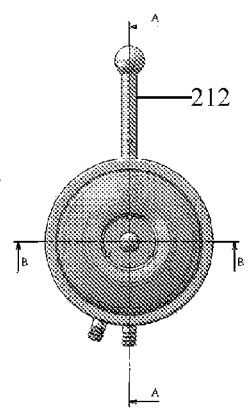
FIG. 25 is an end view of the machining tool of FIG. 24.
Figure 26:
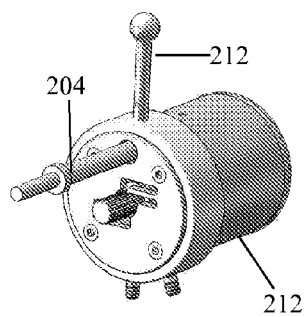
FIG. 26 is a perspective view of the machining tool of FIG. 24.
Figure 27:
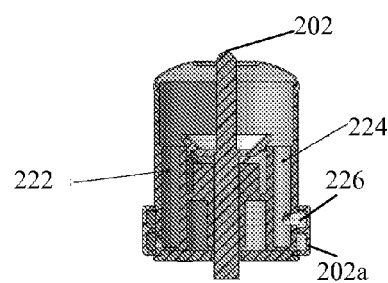
FIG. 27 is a section on line B-B of FIG. 24.
Figure 28:
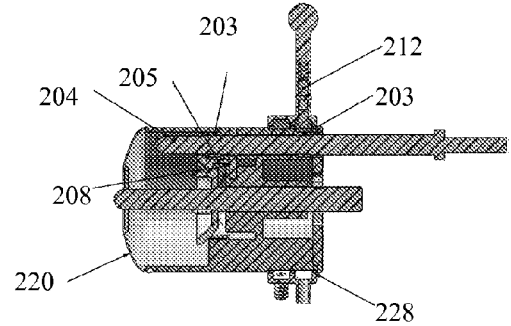
FIG. 28 is a section on line A-A of FIG. 24.
Figure 29:
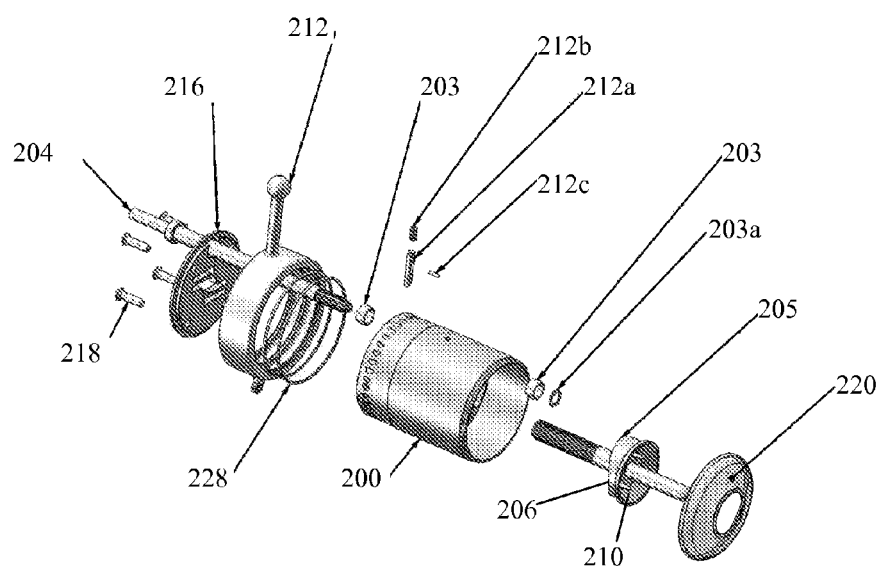
FIG. 29 is an exploded view of the machining tool of FIG. 24.

Referring to FIGS. 21 to 23, the acetabular cup 100 is of substantially constant thickness and part spherical, with a rim 110 which is contoured so as to correspond in some ways to the rim of the acetabulum itself, but also so as to be simple to manufacture. The rim therefore is continuously curved and has raised and lowered regions forming an acetabular notch 112 an anterior pubic eminence 114, an ischial eminence 116 an iliac eminence 118 and an iliopubic interval 120. Measured from a reference plane passing through the cup centre and parallel to the plane which is the RMS best fit through the points on the cup rim the acetabular notch has a depth of at least 15° and preferably at least 20° below the reference plane. The other recesses have a depth of at least 5° from the reference plane, and preferably at least 10°. However, since the cup is less than hemispherical, the recesses have greater depth from the reference plane than the eminences have height. The iliac and ischial eminences therefore preferably rise to at least 5° above the reference plane, but at least to level with the reference plane, and the pubic eminence preferably rises at least to the reference plane, or at least to within 10° of the reference plane. Defining the depth of a recess as the difference between the subtended angle at the bottom of the recess and the average angle of the two eminences on either side of it, the depth of each of the ilio-pubic and ilio-ischial intervals is preferably at least 10° and the depth of the depth of the acetabular notch is preferably at least 20°.

The femoral head implant 102 comprises a part spherical cap 130, the outer surface of which is arranged to bear against the inner surface of the acetabular cup 100. The internal surface of the cap 130 can take a variety of shapes, but in this embodiment has a flat area 131a at the bottom, a part conical area 131b extending outwards from the flat bottom 131a, and a cylindrical part 131c extending up from the outer edge of the part conical area to the rim of the cap. A fixing post 132 projects from the centre of the flat bottom up and approximately through the centre of curvature of the bearing surface. The post 132 extends out beyond the rim of the cap 130. The rim of the cap 130, and hence also the external bearing surface, varies in height, with extended regions 134, 136 on the anterior and posterior sides, and between these, recesses on the medial and lateral sides. The subtended angle is about 120° to 125° at the extended regions and about 100 to 110° at the recesses. Therefore each of the extended regions subtends and angle of at least 10° greater than each of the recesses to either side of it, an in this case at least 15° greater. Taking the depth of each of the recesses as being the difference between the subtended angle at the bottom of the recess and the average subtended angle of the two extended regions on either side of it, the depth of each of the recesses is preferably at least 10°, and may be at least 15°. This shape is arranged so as to replace only bone that is typically covered by articular cartilage and also to prevent soft tissue damage and to provide adequate clearance and protection for blood vessels, while providing sufficient bearing support in the anterior and posterior sides.

It will be appreciated that the important part of the femoral head implant is the bearing surface. The internal surface and support can be designed in a number of different ways. In a further embodiment the design of the acetabular cup is substantially simplified, and it includes an acetabular notch, which is symmetrical about its centre point, with the rest of the rim being flat. Referring to FIG. 17, if the position on the cup is defined as an angle from a point to be located at the anterior landmark on the acetabulum, the cup is symmetrical about a point at approximately 290°. This has two advantages. Firstly it is simple to manufacture, and secondly because it is symmetrical, the cup is non-handed, and the same shape of cup can be used on both the left and right hips.

Figure 42:
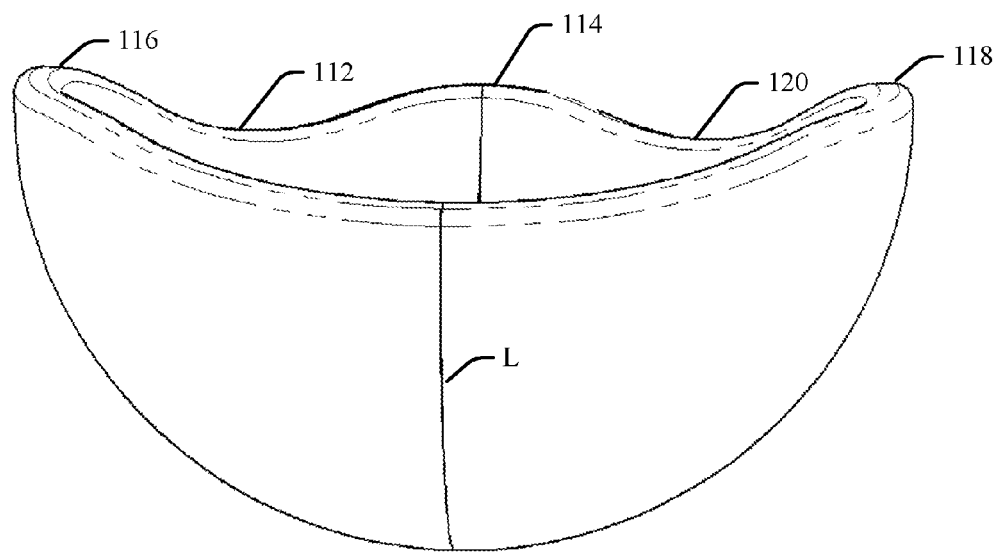
FIG. 42 is a side view of an acetabular cup implant for use in a hip.
Figure 43:
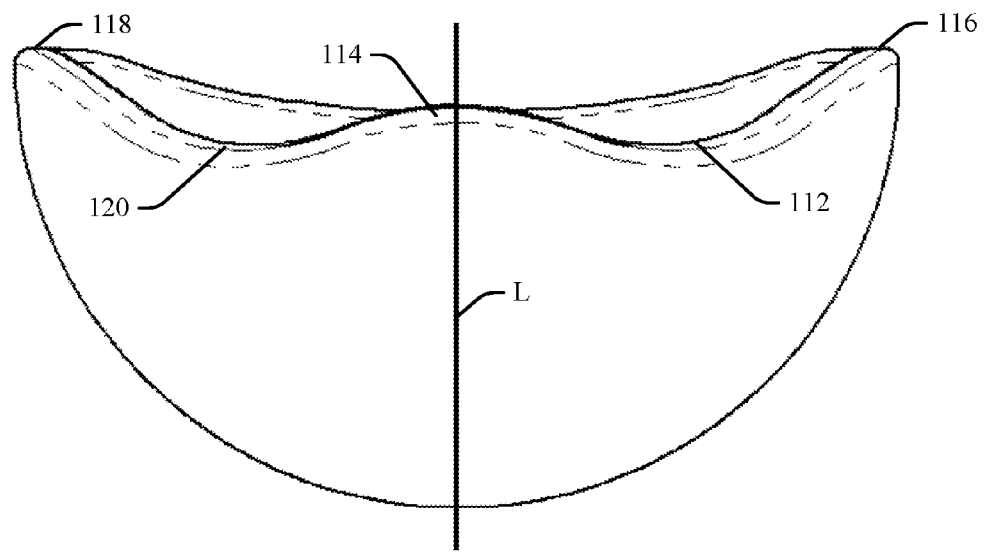
FIG. 43 is a side view of the acetabular cup implant for use in a hip of the type shown in FIG. 42.

In a still further embodiment, as shown in FIGS. 42-43, and still referring to FIG. 17, the cup includes a symmetrical ilio-ischial interval centred on a point of symmetry at about 160° on the rim, iliac and ischial eminences 118, 116, respectively, located symmetrically on either side of the point of symmetry line L, an ilio-pubic interval 120 and an acetabular notch 112 also arranged symmetrically about the centre of the ilio-ischial interval, and a pubic eminence 114 symmetrically located directly opposite the ilio-ischial interval. In each case the eminences extend beyond a reference plane of the cup, which is the best fit plane through all points on the rim, and the intervals and notch dip below that plane.

The femoral head implant as shown is not symmetrical, but in another embodiment, this implant can also be made symmetrical, with the anterior and posterior extensions 134, 136 being symmetrically placed on opposite sides of the rim and each being symmetrical about its own centre. Again this allows for the same implant to be used on both left and right hips.

A complete set of implants will include a number of pairs of matching implants, the pairs being of different sizes to fit different patients. However, the shape of the different pairs is identical, the only difference being of scale.

Referring to FIGS. 24 to 29 a machining tool for machining the femur to the correct shape to receive the femoral cap 102 comprises a cylindrical body 200 with a locating pin 202 aligned with its axis and projecting from its front end. A cutter 204 is supported on bearings 203 in the body 200 parallel to the locating pin 202 and offset from the location axis. The locating pin 202 has a cam 205 support coaxially around it, with a rearward facing cam surface 206, having a height that varies in the axial direction. As can best be seen in FIGS. 27 and 28 the body 200 has a forward facing cam follower surface 208 formed within it which is arranged to contact the cam surface 206 and to cause the body 200 to move axially relative to the locating pin 202 as the body is rotated about the locating pin. Spikes 210 in the front of the front of the cam 205 are provided to secure the locating pin 202 in rotation with the femur. The cutter 204 is slidable axially in the body 200 and is supported in the bearings 203 so that it can be rotated to cut the femur. The forward movement of the cutter 204 through the body 200 is limited by a collar 204a on the cutter. A ratcheting lever 212 projects radially from a rear section 202a of the body 200 to enable a user to rotate the body 200 and cutter about the location pin 202. The rear end of the body 202 is closed by a cover 216 held in place by screws 218. A flexible gaiter 220 at the front end of the body 200 is arranged to seal the body against the femur. The body 202 is hollow and irrigation ports 222, 224 are provided in the rear section 202a. Irrigation passages 226 are formed between the rear body portion 202a and the main body portion 202b to connect a saline solution irrigation system, which can be connected to the ports 222, 224, to the interior of the body to irrigate the cutter 204. Ring seals 228 seal these passages from each other. The tool may further comprise a navigation device, such as an optical navigation device, to enable it to be orientated correctly relative to the bone.

Figure 31:
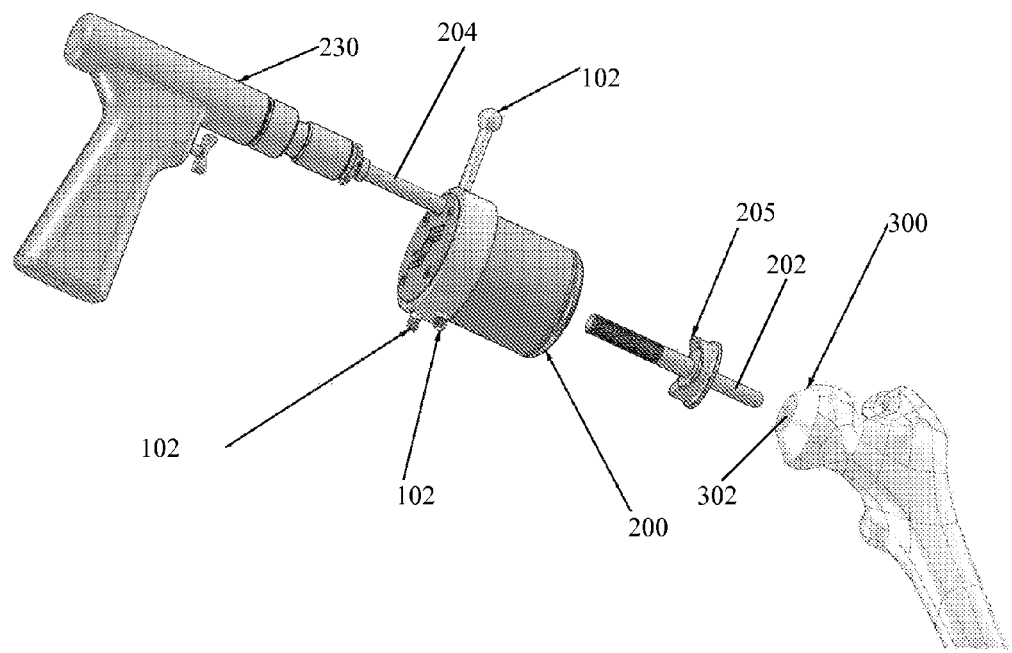
FIG. 31 shows the machining tool of FIG. 24 in use.

Referring to FIG. 31 in use the head of the femur is first pre-machined to form a shallow conical surface 300 on its end and a bore 302 extending inwards from its end, approximately along the neck axis. The locating pin 202 is inserted into the bore 302 and the spikes 210 on the back of the cam 205 pushed into the machined surface 300 to fix the locating pin 202 and the cam 205 in rotation The body 200 is then placed over the location pin 202 and pushed forwards until the cam follower surface 208 in the body contacts the cam surface 206. A high speed drill 230 is connected to the cutter 204 and the cutter driven and pushed forwards through its bearings to machine the bone until the collar 204a on the cutter limits the axial forwards movement of the cutter 204. The body 202, cutter 204 and drill 300 are then rotated about the locating pin 202, while the cutter 204 is pushed forwards, so that the cutter is moved axially by virtue of the cam 205 to cut the femur to the correct shape to receive the femoral head implant 102.

Figure 30:
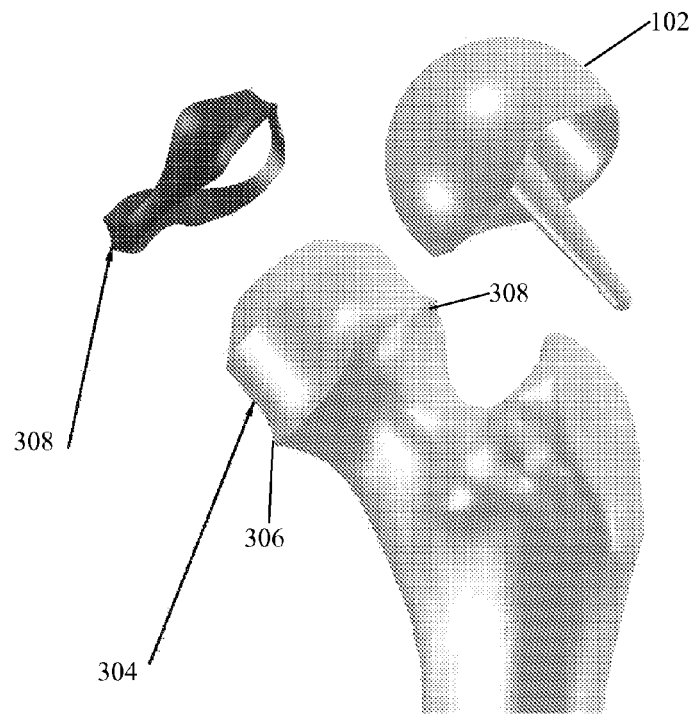
FIG. 30 is an anterior view of a femoral head machined according to an embodiment of the invention.

Referring to FIG. 30, it will be appreciated that the cam surface 206 is shaped to correspond to the shape of the rim of the femoral head implant 102. This results in the head of the femur being cut so that it has a cylindrical portion 304 extending back from the top end of the femur. The bottom edge 306 of the cylindrical portion is contoured so as to be deeper on the anterior and posterior sides and shallower at the superior and inferior sides It is an advantage of this method that only the minimum amount of the femur is cut away to allow the femoral head implant 102 to be inserted. As shown in FIG. 30 there is a volume 308 of bone below the machined cylindrical portion, which is wider than the cylindrical portion. This maintains strength in the bone, and also supports and locates the implant.

Figure 32:
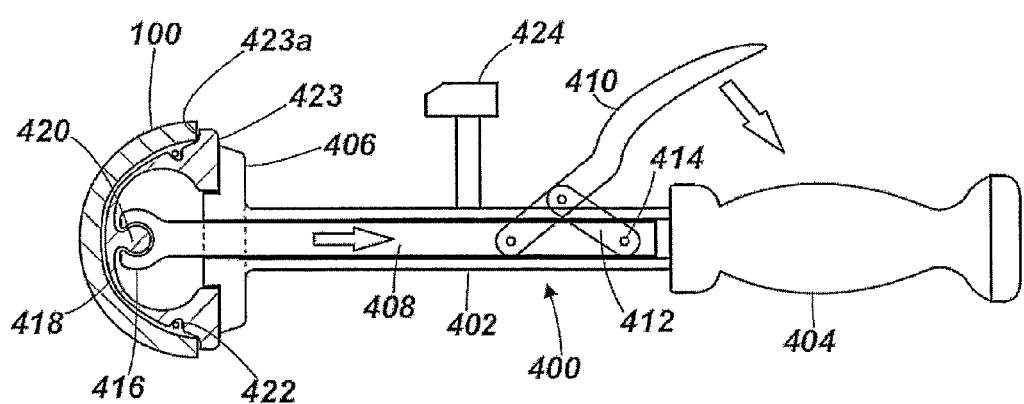
FIG. 32 is a section through an insertion tool for acetabular cup implants according to an embodiment of the invention.

Referring to FIG. 32, an insertion tool 400 for use with the acetabular cup 100 comprises a hollow shaft 402 with its rear end supported in a handle 404 and a flange 406 at its front end. A sliding rod 408 is located within the shaft 402 with its front end projecting from the front end of the shaft furthest from the handle, in the centre of the flange 406. An operating lever 410 is pivotably mounted on the shaft 402, and a drive link 412 is connected between the lever 410 and the sliding rod 408, to which it is connected by a pin 414 which extends through a slot down one side of the shaft 402. The drive link 412 and pin 414 therefore move the rod 408 along the shaft 402 as the lever 410 is pivoted on the shaft 402. The front end of the sliding rod 408 has a gripping device 416 on it. A resilient cup 418, for example of moulded elastomeric material, is placed over the front end of the tool, with its rim resting on the flange 406. A protuberance 420 in the centre of the inside surface of the cup 418 is arranged to be gripped by the gripping device 416. Near the base of the outer surface of the cup, a groove 422 is formed extending around the cup, and an O-ring seal is located in this groove 422. At the rim of the cup 418 a flange 423 is formed on its outer side, the front side 423a of which is contoured so as to match the contoured rim of the acetabular cup 100. This provides rotational location of the acetabular cup 100 on the tool 400. A navigational location device 424 is mounted on the shaft 402 which can be used to determine the location and orientation of the tool, and hence of the acetabular cup 100.

In use, the resilient cup 418 is placed inside the acetabular cup implant 102 so that the O-ring seals against its inner surface. The operating lever 410 is then moved backwards which pulls the sliding rod 408 backwards. This pulls the base of the resilient cup 418 away from the implant cup 100 creating a vacuum between them, so that the implant cup 100 can be picked up and moved with the tool. The exact position of the implant cup 100 can be monitored using the navigational device 424, and the implant cup moved to its desired position and then released using the operating lever.

Figure 33:
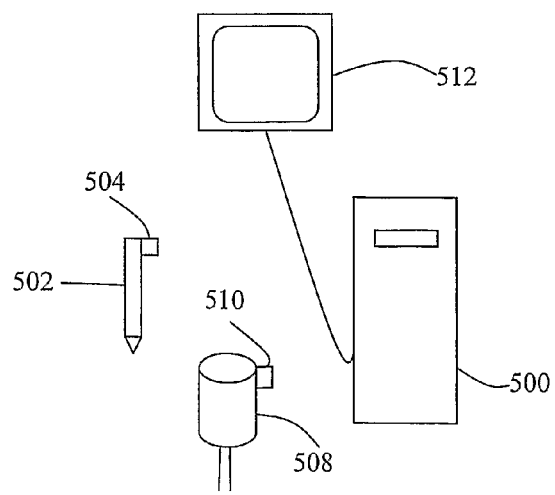
FIG. 33 is a schematic diagram of a surgical guidance system according to an embodiment of the invention.

Referring to FIG. 33, during an operation to resurface a patient's hip, a surgical guidance system is used. This includes a processing system and associated memory in the form of a computer 500 running a guidance program. A bone location device 502 can be attached to a bone and is arranged to communicate its position and orientation via an optical or other tracking device 504 to the computer 500. This provides a reference position and orientation in real space. The femoral machining tool 508 is also provided with a tracking device 510 so that its position and orientation can be determined by the computer. The acetabular cup insertion tool 400 is also set up so that its navigation device 424 provides the tracking output whereby the computer 500 can determine its position and location. In an alternative to this arrangement a CTN system (Acrobot Co Ltd of London UK) can be used which uses tracking arms to locate the tools and bone. The guidance program is arranged to use images of the pelvis and femur to enable a user to input reference locations on those bones, and from those reference positions to determine a desired position for the implants.

The patient is scanned and images of the pelvis and the femur are analysed to locate the hip centre and determine the location and orientation of the acetabular plane in the pelvis relative to the reference position and orientation using the coordinate system of FIGS. 4 to 7, which is fixed relative to the bone, and also the size of the acetabulum, for example as a mean radius. The location in the image of the landmark features of the bones, relative to which the target positions of the implants can be determined, can be identified by a user using an input device such as a mouse. Alternatively the computer processor can in some cases locate the landmark features in the images using image processing techniques. From these positions the size of the implants to be used is determined, and the desired position and orientation of the acetabular cup implant determined using chosen values for the horizontal, vertical and posterior scaled offsets.

Similarly the scan images are used to locate the neck centre line, and head/neck junction plane on the femur using the method described above with reference to FIGS. 9 to 16. From these, the desired position of the centre, and the orientation, of the femoral head implant, relative to the reference position in the frame of reference of the bone, can be chosen. It should be noted that the desired position of the head implant is determined relative to features of the femoral neck, so that wear of the femoral head will not affect the chosen position of the implant.

In order to carry out the resurfacing, the bone location device 502 is attached to the bone, which enables the computer 500 to determine the absolute position of the bone, and hence, from the images, which include the location device and hence the reference position, the absolute desired position and orientation of the implants. The machining tool is controlled by the surgeon, while the computer monitors its position and provides feedback to the surgeon via the screen 512 to guide him so that he can position the machining tool so as to machine the bone correctly to achieve the desired position and orientation of the implant.

Figure 34:
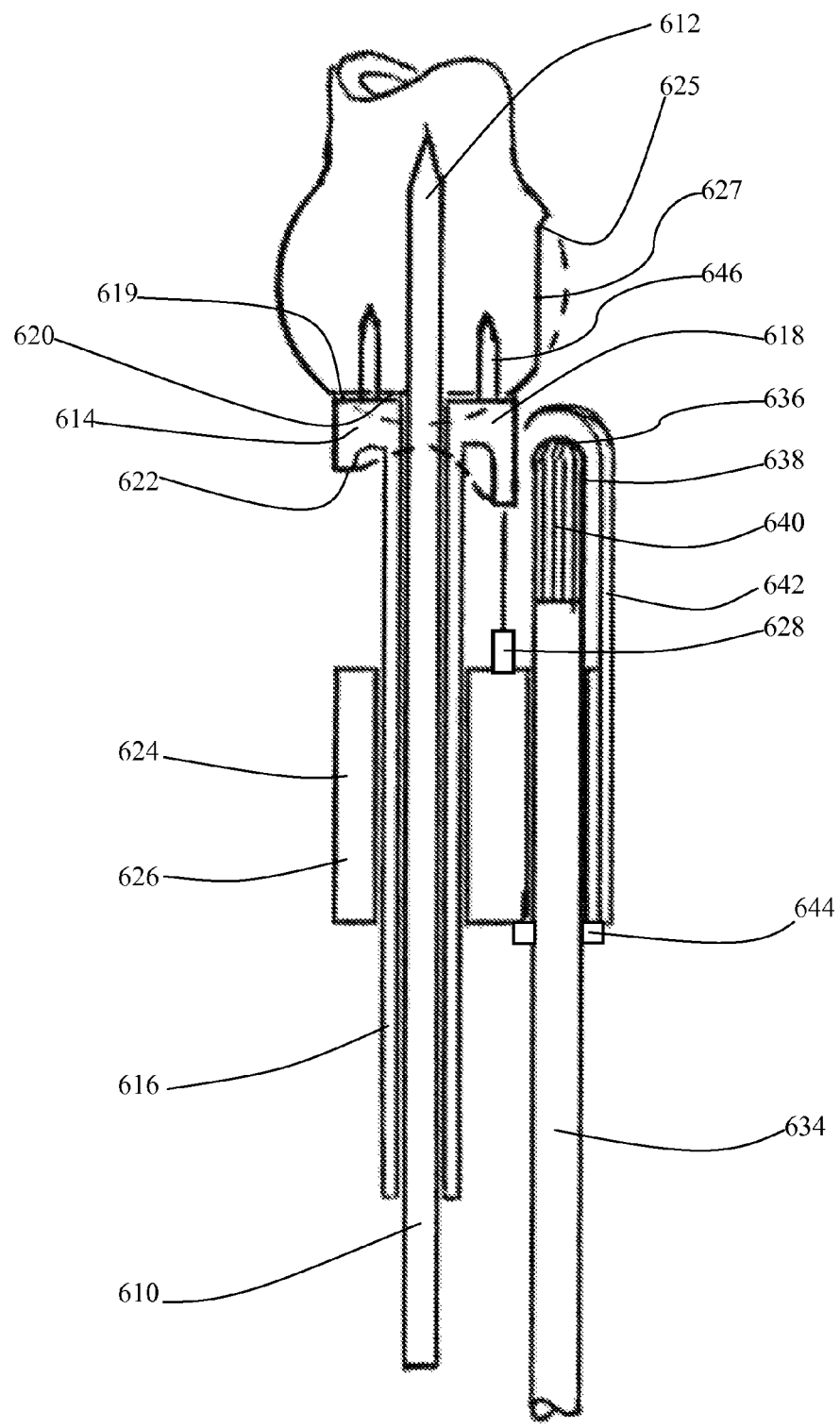
FIG. 34 is a section through a cutting tool according to a further embodiment of the invention for cutting a femoral head in preparation for an implant.

Referring to FIG. 34, a machining tool according to a further embodiment of the invention for machining a femoral head comprises a central guide pin 610 which is sharpened at its front end 612. A cam guide 614 comprises a tubular portion 616 which is a sliding fit around the guide pin 610, with a head 618 at its front end. The head 618 has a flat annular front surface 619 arranged to locate against a corresponding annular surface 620 formed on the femoral head, and a rearward facing cam surface 622 on its rear side. The cam surface 622 is annular, extending around the guide pint 610, and varying in height, i.e. distance from the flat front surface 619. A radius block 624 comprises a short tubular portion 626 which is slidably mounted on the tubular portion 616 and has a cam follower 628 projecting axially from its front end and arranged to contact a point on the cam surface 622. The radius block further comprises a cutter support portion 630 which has a bore 632 through it parallel to the guide pin 610 in which a cutter 634 is supported. The cutter 634 is in the form of a long cylindrical bit with a cutting tip 636 at its front end and a cutting surface 638 extending around a cutting portion 640 which extends back from the front end. The cutter 634 is supported at a fixed distance from the guide pin 610 and can be rotated about the guide pin 610 to cut the femur. A semi-cylindrical cutter shield 642 is mounted on the radius block 624 and projects forward from it so as to cover the outside of the front part of the cutter 634. A collar 644 on the cutter limits its movement forward through the radius block, so that the cutter can be moved forward to a fully inserted position where it is just spaced from the front end of the cutter shield 642.

In use, the top surface of the femur is cut to form the flat surface 620, and the guide pin 610 is inserted into the femoral head so that it projects perpendicular to the flat surface 620. The cam 614 is then slid down over the guide pin 610, and orientated so that the cam surface 622 is correctly orientated relative to the bone. The cam guide is then pushed forward so that location pins 646 on its front end lock into the bone to secure the cam guide in position. The radius block 624 is then pushed forwards until the cam follower 628 locates on the cam surface 622. The radius block 624 is then rotated so that the sides of the femoral head are cut away to the desired depth, the depth of the cutting, and therefore the height of the bottom edge 625 of the cut-away portion 627 varying around the femoral head as dictated by the profile of the cam surface 622.

Figure 35:
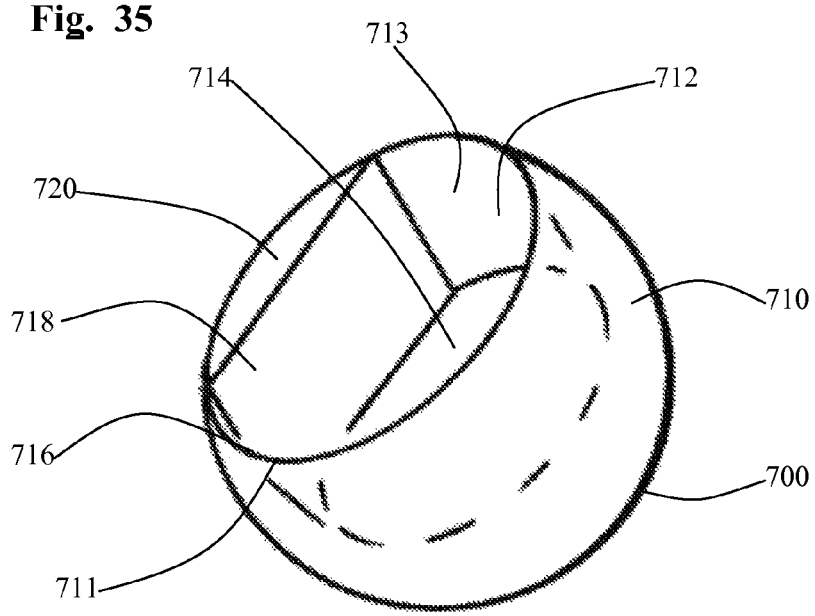
FIG. 35 is a perspective view of a femoral head implant according to a further embodiment of the invention.

Referring to FIG. 35, a femoral implant 700 according to a further embodiment of the invention is similar to that of FIG. 22 in that it has a part spherical outer surface 710 with an internal cavity 712 inside it arranged to fit over the cut part of the femoral head after it has been machined, for example using the machine tool of FIG. 34. The edge 711 of the part spherical outer surface will vary in height around its edge in the same way as the femoral implant of FIG. 22, but that is not shown in FIG. 35. In this case the cavity 712 is generally cylindrical, having a curved internal surface 713 with its bottom end 714 closed and its top end 716 open to receive the machined part of the femoral head. However, one side 718 of the cavity is flat, with the cavity being partially filled in, so that the volume of the cavity is less than a fully cylindrical cavity. Therefore, even though the axis of the cylindrical part of the cavity is aligned with the centre of the part spherical outer surface, the wall 720 of the implant in the region of the flat side surface 718 of the cavity is thicker than the rest of the wall of the implant, which is constant around the curved side wall 713 of the cavity.

The implant of FIG. 35 can be used in cases where the femur is severely worn to such an extent that there is insufficient bone in place to be cut into a full cylinder to support the implant, when the implant is correctly positioned on the femur. With cam-type hip deformities, one side of the femur is extremely worn. In such cases the femur can be cut to leave a part cylindrical volume of bone to support the implant, but with one face, where insufficient bone was present to form a complete cylinder, cut away to correspond with the flat wall 718 of the cavity 712.

Figure 36:
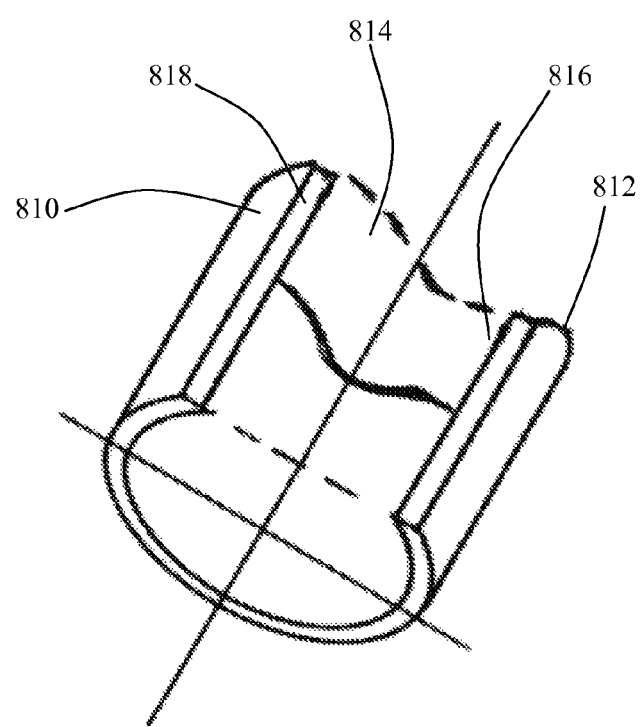
FIG. 36 is a perspective view of a cutting guide for use in cutting a femoral head in preparation for the implant of FIG. 35

Referring to FIG. 36, a cutting guide 800 for use with the implant of FIG. 35 comprises a part-tubular sleeve 810, with one end 812 contoured to fit against the contoured lower edge 625 of the cut-away portion of the femur. One side 814 of the guide is cut away leaving a gap 816 between two axially extending end faces 818. The end faces 818 are in a common plane which is parallel to, but offset from, the axis of the guide. The interior surface of the guide 800 is the same size and shape as the curved interior surface 713 of the implant 700, with the gap 816 having a width equal to that of the flat internal surface 718 of the implant 700.

In use, when the femur has been cut with the machine tool of FIG. 34, the cut portion of the bone may not be a complete cylinder if one side of the femoral head has been worn away to a level inside the radius at which the cutter cuts. In that case, the guide 800 is placed over the cut bone so that the gap 816 is aligned with the non-cylindrical part of the cut bone. The bone is then cut down to a flat plane level with the end faces 818 of the guide 800. This leaves a part cylindrical cut bone portion which corresponds to the shape of the cavity 712 in the implant. The implant can then be put in place over the cut bone portion, and the cavity in the implant will be completely filled with bone so that the implant is securely supported on the femur. It will be appreciated that the exact shape of the cavity in the implant can vary. For example a set of implants and guides could be used to accommodate different levels of wear on the femur, to maximize the amount of bone left in each case while ensuring that the implant cavity is completely filled with bone in each case. Alternatively the cavity in the implant could be cylindrical, but offset from the centre of the part-spherical external bearing surface. This would still result in the wall of the implant varying in radial thickness around the cavity, for example around the side of the cavity at a fixed height above the bottom of the cavity. In some cases it is advantageous to have a set of implants all of which have the same shaped internal cavity, but with the cavities being of different sizes, while the external bearing surfaces are the same size. The implants will therefore have walls of different thicknesses. This allows an implant to be selected to match the size of the femoral head that is being re-surfaced.

Figure 37:
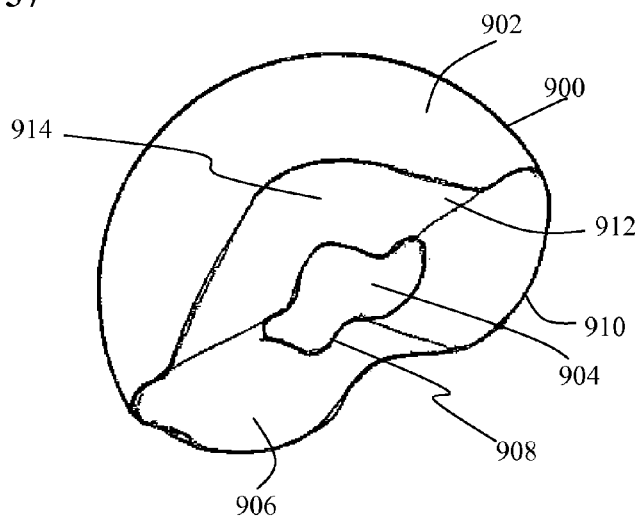
FIG. 37 is a perspective view of an acetabular cup implant according to a further embodiment of the invention.

Referring to FIG. 37, an acetabular cup implant 900 according to a further embodiment of the invention is similar to that of FIGS. 21 to 23, but in this case the wall 902 of the cup is much thicker. Although the wall thickness can vary, in this case it is greater than the radius of the part-spherical inner bearing surface 904. This means that the implant can be used with a femoral head implant with a bearing surface which has a much smaller radius of curvature than that of FIGS. 21 to 23. In the embodiment of FIG. 37 the rim 906 of the cup is contoured in the same way as that of the embodiment of FIGS. 21 to 23, with the inner and outer edges 908, 910 of the rim following the same contours so that the three eminences 912 and the three recesses or intervals 914 are present across the full width of the cup wall.

Figure 38:
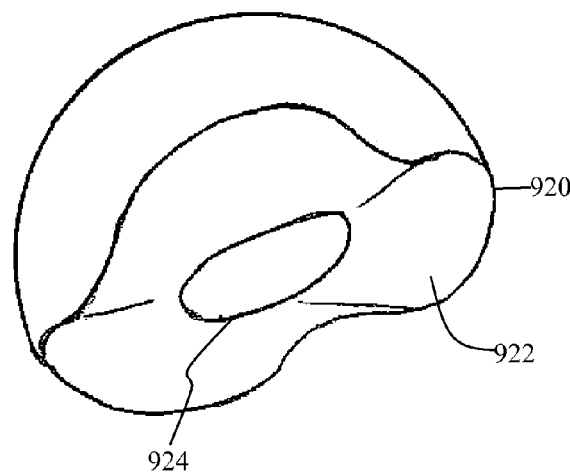
FIG. 38 is a perspective view of an acetabular cup implant according to a still further embodiment of the invention.

Referring to FIG. 38, in a further embodiment the outer edge 920 of the rim 922 again follows the same anatomical contours with the same three eminences and intervals, but the inner edge 924 of the rim is flat and defines a circle. The height of the internal bearing surface 926 is therefore constant around its edge. The contoured shape of the rim 922 of the cup blends gradually from its outer edge 920 to its inner edge 924 with the height of the eminences and recesses gradually reducing from the outer edge 920 to the inner edge 924. This has the advantages of maximizing the bearing area of the internal bearing surface, reducing contact area stress and reducing the risk of dislocation. It will be appreciated that the inner edge 924 can have a degree of contouring that is not zero, but less than that of the outer edge 920.

Figure 39:
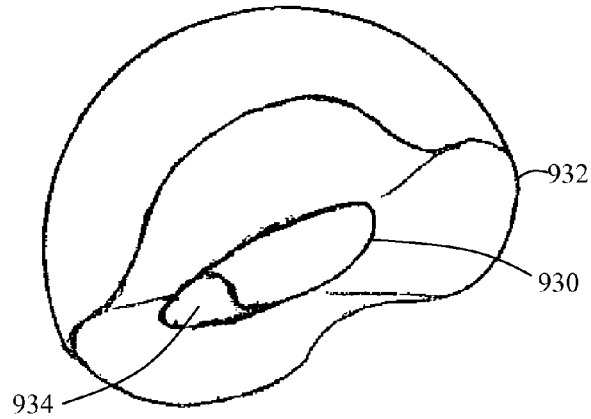
FIG. 39 is a perspective view of an acetabular cup implant according to a still further embodiment of the invention.

Referring to FIG. 39, in a further embodiment the inner edge 930 of the rim is not flat, but still contoured in a way that is different from the outer edge 932. The angular positioning of the contours is different at the inner edge 930 from the outer edge 930. This allows the outer edge 932 to be contoured so as to provide the best anatomical fit as with the embodiments described above, and the inner edge 930 to be contoured so as to maximize the range of movement of the femoral implant relative to the cup before impingement occurs between the side of the neck of the femoral component and the inner edge 930 of the rim of the cup. For example in this embodiment the inner edge 930 is flat around most of its circumference but has a single recess 934 cut away to reduce neck impingement in deep flexion. As with the embodiment of FIG. 38, the contouring of the rim blends gradually between the outer edge 932 and the inner edge 930. It will be appreciated that the number and angular location of the recesses and eminences at the inner edge 930 can vary in a number of different ways independently of the contours of the outer edge 932. In some cases it is also possible to have a cup design which includes features from two or three of the designs of FIGS. 37 to 39, for example having different designs at different points around the rim of the cup.

Figure 40:
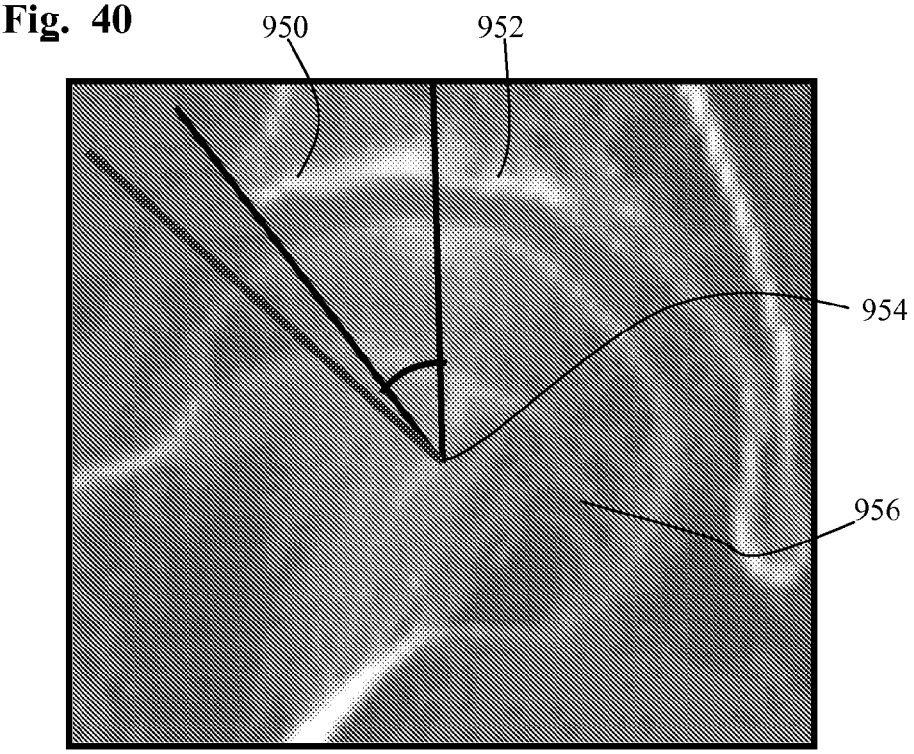
FIG. 40 is an image of a female hip join showing a worn acetabulum.
Figure 41:
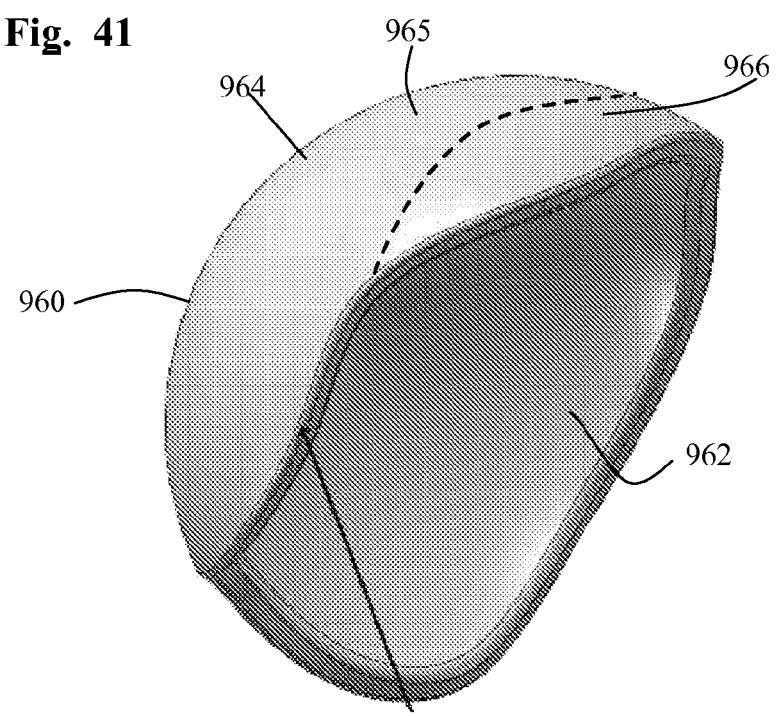
FIG. 41 is a perspective view of an acetabular cup implant for use in a hip of the type shown in FIG. 40.

Referring to FIG. 40, it is common in female hips with a normal or slightly dysplastic pelvis for the superior lateral region 950 of the acetabulum 952 only to extend about 35°, measured as an angle at the hip centre 954, in the lateral direction from the vertical direction V. This can provide insufficient support for the femoral head 956. Referring to FIG. 41, an acetabular cup implant 960 designed for use in such hips has an inner bearing surface 962 that is part spherical and of constant radius of curvature, but an outer surface 964 that comprises two main regions 965, 966 having different functions. The largest region 965 is a bone interface region arranged to be placed in contact with the bone of the pelvis when the implant is in place. The smaller region 966 is an extension region which extends along the superior edge of the outer surface 964, being widest at the highest point on the rim and tapering towards its anterior and posterior ends. The extension region 966 is arranged to encourage the growth of the pelvic bone at the rim of the acetabulum over it, so as to increase the strength of the acetabulum and the support it provides for the implant. This extension region 966 may have the same characteristics as the bone interface region 965, i.e. the same surface texture and radius of curvature, and may therefore comprise an extension of the bone interface region. However in some embodiments it has different characteristics. In some cases it may have a different radius of curvature from the bone interface region. In some cases it may have a different surface texture designed to encourage bone growth over it. In this embodiment the extension region 966 is smooth on the macro- and micro-scale, i.e. at a scale of several microns, e.g. 10 microns or above, having no surface features of that size. In some cases it may have no surface features which are larger than 1 micron. It is however rough on the nanometer scale, i.e. having surface features which are less than 1 micron in height. In some cases it may only have surface features which are 500 nm in height or smaller. This is different from the bone interface region 965 which in this embodiment is rough on the scale greater than 1 micron, but could be rough on a scale of 10 microns, or 100 microns or on larger macro-scales to provide an interference fit with the bone. In other embodiments the bone interface region can be less rough, or rough only on a smaller scale, than the extension region.

The invention claimed is:

1. An acetabular cup implant comprising a part-spherical cup, the part-spherical cup having a rim which varies in height around the cup so as to comprise at least three raised regions and at least three lowered regions, the raised regions separating the lowered regions from each other so that the lowered regions define a first recess for location between the pubis and the ischium, and at least two further recesses, separate from the first recess, and the height of the cup varies symmetrically about a point on the rim, so that identical implants can be used for left and right hips.

2. A method of positioning an acetabular cup implant in a pelvis comprising locating a plurality of reference points on the pelvis, defining a target location of the implant relative to the reference points, and placing the implant at the target location, wherein the acetabular cup implant comprises a part-spherical cup, the part-spherical cup having a rim which varies in height around the cup so as to comprise at least three raised regions and at least three lowered regions, the raised regions separating the lowered regions from each other so that the lowered regions define a first recess which is located between the pubis and the ischium, and at least two further recesses, separate from the first recess, and the height of the cup varies symmetrically about a point on the rim, so that identical implants can be used for left and right hips.

3. A method according to claim 2 wherein the target location is defined in terms of a target position and a target orientation of the implant.

4. A method according to claim 2 wherein at least one of the further recesses includes a recess which is located between the pubis and the ilium.

5. A method according to claim 4 wherein at least one of the further recesses includes a recess for location between the ilium and the ischium.

6. A method according to claim 5 wherein the rim is raised to form an ischial facet for location in the region of the ischium.

7. A method according to claim 2 wherein at least one of the further recesses includes a recess which is located between the ilium and the ischium.

8. A method according to claim 2 wherein the rim is raised to form an ischial facet which is located in the region of the ischium.

9. A method of positioning an acetabular cup implant in a pelvis comprising locating a plurality of reference points on the pelvis, defining a target location of the implant relative to the reference points, and placing the implant at the target location, wherein when placed at the target location the acetabular cup implant comprises a part-spherical cup, the part-spherical cup having a rim which varies in height around the cup so as to comprise at least three raised regions and at least three lowered regions, the lowered regions defining a first recess which is located between the pubis and the ischium and at least two further recesses, and the height of the cup varies symmetrically about a point on the rim, so that identical implants can be used for left and right hips without modification to the implant.

10. A method of positioning an acetabular cup implant in a pelvis comprising locating a plurality of reference points on the pelvis, defining a target location of the implant relative to the reference points, and placing the implant at the target location, wherein the acetabular cup implant comprises a part-spherical cup, the part-spherical cup comprising a rim including an outer edge which varies in height around the cup so as to comprise at least three raised regions and at least three lowered regions, the raised regions separating the lowered regions from each other so that the lowered regions define a first recess for location between the pubis and the ischium, and at least two further recesses, separate from the first recess, and the height of the cup varies symmetrically about a point on the rim, so that identical implants can be used for left and right hips.

11. A method according to claim 10 wherein the rim of the cup also has an inner edge and the variations in height around the rim at the inner edge are different from the variations in height at the outer edge.

12. A method according to claim 11 wherein the variations in height are less at the inner edge than at the outer edge.

13. A method according to claim 12 wherein the variations in height at the inner edge are substantially zero.

* * * * *